United States Patent
Hasegawa et al.

(10) Patent No.: US 9,486,755 B2
(45) Date of Patent: Nov. 8, 2016

(54) PRODUCTION METHOD OF A POWDER COSMETIC

(75) Inventors: Shuji Hasegawa, Yokohama (JP); Masaki Bundo, Tokyo (JP); Koutaro Oota, Tokyo (JP); Takuma Kurahashi, Yokohama (JP); Keisuke Touyama, Yokohama (JP); Katsuki Ogawa, Yokohama (JP); Yoshito Ogura, Yokohama (JP)

(73) Assignee: SHISEIDO COMPANY LTD., Tokyo (JP)

( * ) Notice: Subject to any disclaimer, the term of this patent is extended or adjusted under 35 U.S.C. 154(b) by 369 days.

(21) Appl. No.: 12/808,191

(22) PCT Filed: Dec. 19, 2008

(86) PCT No.: PCT/JP2008/073238
§ 371 (c)(1),
(2), (4) Date: Jun. 15, 2010

(87) PCT Pub. No.: WO2009/078486
PCT Pub. Date: Jun. 25, 2009

(65) Prior Publication Data
US 2010/0266519 A1    Oct. 21, 2010

(30) Foreign Application Priority Data

Dec. 19, 2007   (JP) ................. 2007-327794

(51) Int. Cl.
*A61K 8/37* (2006.01)
*A61K 8/81* (2006.01)
(Continued)

(52) U.S. Cl.
CPC ........... *B01F 7/00858* (2013.01); *A61K 8/37* (2013.01); *A61K 8/375* (2013.01); *A61K 8/8111* (2013.01);
(Continued)

(58) Field of Classification Search
CPC ...... A61K 8/37; A61K 8/375; A61K 8/8111; A61K 8/891; A61K 8/92; A61Q 1/12; B01F 3/1221; B01F 7/00858; B01F 2215/0481
See application file for complete search history.

(56) References Cited

U.S. PATENT DOCUMENTS

| | | |
|---|---|---|
| 4,374,796 A | 2/1983 | Ogasawara et al. |
| 4,403,932 A | 9/1983 | Ogasawara et al. |

(Continued)

FOREIGN PATENT DOCUMENTS

| | | |
|---|---|---|
| JP | 56-127305 | 10/1981 |
| JP | 58-82839 | 6/1983 |

(Continued)

OTHER PUBLICATIONS

JPO Machine translation of JP, 2007-055990,A, (Hata et al.) accessed at http://www4.ipdl.inpit.go.jp/Tokujitu/tjsogodbenk.ipdl on Jul. 1, 2014.*

(Continued)

*Primary Examiner* — Kortney L. Klinkel
*Assistant Examiner* — Lisbeth C Robinson
(74) *Attorney, Agent, or Firm* — Rankin, Hill & Clark LLP

(57) ABSTRACT

A production method for making powder cosmetics having improved characteristics. The method includes mixing a powder component and an oil component as a binder using a mixing apparatus. The mixing apparatus is a facing rotor type mixing apparatus having a first rotor with a plurality of blades and a second rotor with a plurality of blades in a mixing chamber. The first rotor and the second rotor face each other and have rotating shafts on the same axis line. In the facing rotor type mixing apparatus, raw materials are fed into an introduction opening on a first rotor side. The raw materials are mixed by rotating the first rotor and the second rotor in the same or opposite directions to each other, and the mixed raw materials are discharged from a discharge opening on a second rotor side.

18 Claims, 3 Drawing Sheets

(51) Int. Cl.
*A61K 8/891* (2006.01)
*A61K 8/92* (2006.01)
*A61Q 1/12* (2006.01)
*B01F 3/12* (2006.01)
*B01F 7/00* (2006.01)

(52) U.S. Cl.
CPC ............... *A61K 8/891* (2013.01); *A61K 8/92* (2013.01); *A61Q 1/12* (2013.01); *B01F 3/1221* (2013.01); *B01F 2215/0481* (2013.01)

(56) References Cited

U.S. PATENT DOCUMENTS

| | | |
|---|---|---|
| 6,972,129 B1 | 12/2005 | Ogawa et al. |
| 2003/0180535 A1* | 9/2003 | Horino et al. ................ 428/384 |

FOREIGN PATENT DOCUMENTS

| | | |
|---|---|---|
| JP | 61-54766 | 11/1986 |
| JP | 7-277924 | 10/1995 |
| JP | 2003-1127 | 1/2003 |
| JP | 2003-10712 | 1/2003 |
| JP | 2003010712 A * | 1/2003 |
| JP | 2006-136870 | 6/2006 |
| JP | 2006-272098 | 10/2006 |
| JP | 2007-55990 | 3/2007 |
| JP | 2007-291302 | 11/2007 |

OTHER PUBLICATIONS

Japanese Patent Abstract for Publication No. 07-277924 published Nov. 24, 1995, five pages.
Japanese Patent Abstract for Publication No. 2003-001127 published Jan. 7, 2003, 12 pages.
Japanese Patent Abstract for Publication No. 2006-136870 published Jun. 1, 2006, 27 pages.
Japanese Patent Abstract for Publication No. 2007-291302 published Nov. 8, 2007, 23 pages.
Thomson Database Patent Abstract for Japanese Publication No. 2006-385170 published Jun. 1, 2006, two pages.
Thomson Database Patent Abstract for Japanese Publication No. 2008-D73996 published Nov. 8, 2007, two pages.
Thomson Database Patent Abstract for Japanese Publication No. 2003-136501 published Jan. 14, 2003, one page.
Thomson Database Patent Abstract for Japanese Publication No. 2003-135806 published Jan. 7, 2003, one page.
Thomson Database Patent Abstract for Japanese Publication No. 1995-400859 published Oct. 24, 1995, one page.
European Patent Office Abstract for Japanese Publication No. 56127305 published Nov. 6, 1981, one page.
Supplementary European Search Report for Corresponding Appl. No. 08861345 mailed Nov. 26, 2010, eight pages.
Masafumi Imazeki, Development and Problems of the Foundation Make-up which Prevent from Make-up Deteriorating and Oily Shining, Fragrance Journal, Ltd., 2000-5, vol. 28, No. 5, May 15, 2000. (Partial English Translation included).
Japanese Patent Abstract for Publication No. 07-277924, published Oct. 24, 1995, five pages.
Japanese Patent Abstract for Publication No. 2006-272098 published Oct. 12, 2006, sixteen pages.
Japanese Patent Abstract for Publication No. 2007-055990 published Mar. 8, 2007, thirty-three pages.
Japanese Patent Abstract for Publication No. 2003-010712 published Jan. 14, 2003, eleven pages.
Japanese Patent Abstract for Publication No. 56-127305 published Oct. 6, 1981, one page.
Espace Patent Abstract for KR 100352137 published Aug. 27, 2002, one page.
Partial Translation for JP58-82839, two pages.
Explanation of Relevance for US6972129, JP2003-010712A and KR0352137B, one page.
International Search Report for corresponding PCT/JP2008/073238 mailed Mar. 17, 2009, two pages.
International Preliminary Report on Patentability for corresponding PCT/JP2008/073238 mailed Jul. 29, 2010, six pages.
Machine translation for JP Publication No. 2003-010712 published Jan. 14, 2003, nine pages.

* cited by examiner

Example 4

Comparative example 4

PRODUCTION METHOD OF A POWDER COSMETIC

RELATED APPLICATIONS

This application claims the priority of Japanese Patent Application No. 2007-327794 filed on Dec. 19, 2007, which is incorporated herein by reference.

FIELD OF THE INVENTION

The present invention relates to the production method of a powder cosmetic, and in particular, relates to the easy production method of a powder cosmetic having improved practical characteristics such as extensibility on the skin, adhesion, feeling of particulate fineness, and long-lasting property, and having improved impact resistance.

BACKGROUND OF THE INVENTION

Powder cosmetics such as powder foundation can be obtained by molding the powder, wherein an oil component as a binder, surfactant, etc. are added to and mixed with the main powder component. Normally, powder applicators such as a puff, a sponge, and a brush are used for application. The conventional general powder cosmetics have been produced by homogenizing with a hammer mill such as a pulverizer after the powder component and the oil component are mixed with the use of agitation mixers such as a Henschel mixer, Nauta mixer, ribbon blender, and kneader, and by press-molding into a metal or plastic inner tray. Such a conventional method is called a dry process because the powder component and the oil component are mixed without the addition of a solvent.

However, fully satisfactory powder cosmetics have not been obtained, by the above-described conventional dry process, in terms of the practical characteristics such as extensibility on the skin, adhesion, feeling of particulate fineness, and long-lasting property, and in terms of the impact resistance. The cause of this is that the homogenization of the powder component and the oil component is not satisfactory; thus the agglomerated powder component remained, and the oil component may be unevenly distributed in the agglomerated powder.

On the other hand, various production methods or molding methods have been developed, in recent years, to improve the practical characteristics of powder cosmetics. For example, the following wet processes have been proposed: the filling-solidifying method of cosmetics, wherein a solvent such as alcohol is added to a cosmetic base to make a slurry, the slurry is filled in a container, and then the solvent is removed by vacuum suction (refer to patent literature 1); the production method of compact powder makeup cosmetics, wherein the base material containing a specific powder, as a powder component, and oil is added to a solvent to make a slurry, and then the solvent is removed (refer to patent literature 2); and the production method of powdery solid cosmetics, wherein a slurry obtained by mixing, in a solvent, the powder component and the oil component as a binder, is treated with a media agitating mill to uniformly coat the surface of the powder component with the oil component, the solvent is removed, and the press molding is carried out to obtain powdery solid cosmetics (refer to patent literature 3).

However, even by the above-described production methods or molding methods, the practical characteristics such as the feeling of particulate fineness and long-lasting property, and the impact resistance were not satisfactory. Especially, in the wet process, the oil component is uniformly coated over the entire surface of powder. Thus, there has been an issue in that the oil absorptiveness of the powder component decreases drastically, and the long-lasting property against the oil such as sebum is poor. In addition, the solvent removal/drying processes are separately necessary in the above-described wet process. Therefore, not only the process becomes complicated but also there are safety issues and environmental issues.

In order to improve the long-lasting property of powder cosmetics, a powder component whose surface is treated with a fluorine compound having water-repellent and oil-repellent properties has been used. However, the homogenization of the powder component and the oil component was difficult because of the oil-repellent property of the fluorine compound. Thus, the powder agglomeration was easily caused; and the expected improvement effect of long-lasting property could not be achieved. In addition, the feeling in use deteriorated sometimes. In order to provide an excellent texture in use, such as extensibility, spherical elastic powder of silicone, polyurethane, etc. has also been blended. However, there has been an issue in that the impact resistance, in particular, becomes worse because of a difficulty in the homogenization of the powder component and the oil component. Furthermore, in order to improve the adhesion to the skin, long-lasting property, etc., the use of high-viscosity oils has been tried. However, it is very difficult to uniformly disperse high-viscosity oil into the powder by the conventional method. In addition, there has been an issue in that detrimental effects, such as the promoted agglomeration of the powder component, are caused.

Patent Literature 1: Japanese Examined Patent Application Publication No. S61-54766
Patent Literature 2: Japanese Unexamined Patent Publication No. H7-277924
Patent Literature 3: Japanese Patent No. 3608778

DISCLOSURE OF THE INVENTION

Problem to be Solved by the Invention

The present invention was made in view of the above-described conventional art, and the problem to be solved is to provide an easy production method of powder cosmetics having improved practical characteristics such as extensibility on the skin, adhesion, feeling of particulate fineness, and long-lasting property, and having improved impact resistance.

Means to Solve the Problem

The present inventors have diligently studied to solve the above-described problems. As a result, the present inventors have discovered that it is possible to uniformly coat the surface of powder particles with the oil component, without the agglomeration of the powder component, by mixing the powder component and the oil component as a binder with the use of a facing rotor type mixing apparatus with a specific structure, which has not been used in the production of cosmetics in the past; thus the powder cosmetics excellent in the practical characteristics such as extensibility on the skin, adhesion, feeling of particulate fineness, and long-lasting property, and excellent in the impact resistance can be easily produced, thus leading to completion of the present invention.

That is, the production method of a powder cosmetic of the present invention comprises a step of mixing powder component and oil component as a binder with a mixing apparatus, wherein the mixing apparatus is a facing rotor type mixing apparatus having a first rotor with a plurality of blades and a second rotor with a plurality of blades in a mixing chamber, in which the first rotor and the second rotor face each other and have rotating shafts on same axis line, and in the facing rotor type mixing apparatus, raw materials are fed into an introduction opening on a first rotor side, the raw materials are mixed by rotating the first rotor and the second rotor in same or opposite directions to each other, and the mixed raw materials are discharged from a discharge opening on a second rotor side.

In the production method of a powder cosmetic, it is preferable to mix 65 to 97 mass % of the powder component and 3 to 35 mass % of the oil component with respect to the total amount of powder cosmetic. In addition, it is preferable in the production method of a powder cosmetic that the first rotor and the second rotor of the facing rotor type mixing apparatus rotate in opposite directions to each other.

In addition, it is preferable in the production method of a powder cosmetic that the powder component comprises fluorine compound-treated powder. It is also preferable in the production method of a powder cosmetic that the powder component comprises 5.0 to 20.0 mass % of elastic powder with respect to the total amount of powder cosmetic. It is also preferable in the production method of a powder cosmetic that the oil component comprises an oil with a viscosity of 100 to 50000 mPa·s. It is also preferable in the production method of a powder cosmetic that the powder component comprises 5 to 75 mass % of a fluorine compound-treated powder with respect to the total amount of powder cosmetic, and the oil component comprises 0.1 to 10 weight % of an oil with a viscosity of 100 to 50000 mPa·s with respect to the total amount of powder cosmetic.

Effect of the Invention

According to the production method of the present invention, it is possible to uniformly coat the surface of powder particles with the oil component, without the agglomeration of the powder component, by mixing the powder component and the oil component as a binder with the use of a facing rotor type mixing apparatus with a specific structure, which has not been used in the production of cosmetics in the past; thus the powder cosmetic excellent in the practical characteristics such as extensibility on the skin, adhesion, feeling of particulate fineness, and long-lasting property, and excellent in the impact resistance can be easily produced. The production method of the present invention is a dry process in which a solvent is not used when the powder component and the oil component are mixed. Thus, the production process is simple compared with the wet process, and there are few safety issues and environmental issues.

Figure 1:
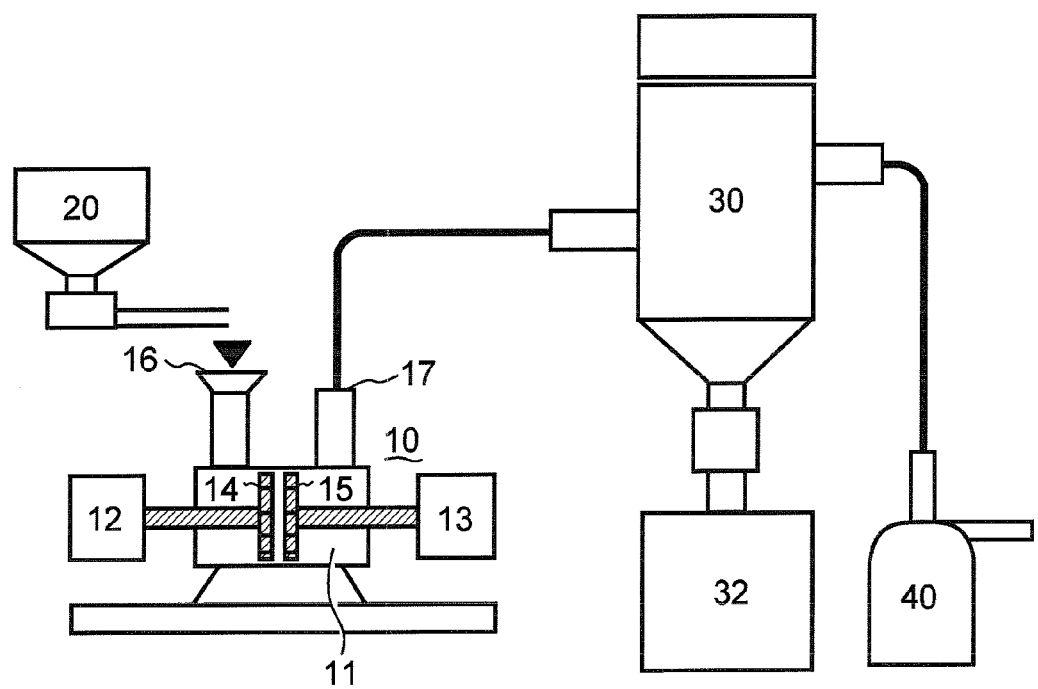
FIG. 1 is a schematic drawing of one example of a facing rotor type mixing apparatus that was used in the production method of the present invention.

DESCRIPTION OF REFERENCE NUMBERS 10 facing rotor type mixing apparatus
11 mixing chamber
12 motor
13 motor
14 first rotor
15 second rotor
16 introduction opening
17 discharge opening
20 raw material supplying device
30 collecting device
32 collection container
40 suction device

BEST MODE FOR CARRYING OUT THE INVENTION

Hereinafter, the embodiment of the present invention will be described in detail; however, the present invention is not limited by these examples.

The production method of a powder cosmetic of the present invention is a method by mixing the powder component and the oil component as a binder. The production method is characterized in that the apparatus for mixing is a facing rotor type mixing apparatus with a specific structure.

Powder Component

The powder component used in the production method of the present invention is not limited in particular so far as the powder is normally used in powder cosmetics. Examples of powder component include talc, kaolin, sericite, muscovite, phlogopite, synthetic mica, lepidolite, biotite, calcined talc, calcined sericite, calcined muscovite, calcined phlogopite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, calcined calcium sulfate (calcined gypsum), calcium phosphate, fluorine apatite, hydroxy apatite, ceramic powder, metallic soaps (for example, zinc myristate, calcium palmitate, and aluminum stearate), boron nitride, photochromic titanium oxide (titanium dioxide with sintering iron oxide), and reduced zinc oxide; organic powders such as silicone elastomer powder, silicone powder, silicone resin-coated silicone elastomer powder, polyamide resin powder (nylon powder), polyethylene powder, poly methyl methacrylate powder, polystyrene powder, styrene/acrylic acid copolymer resin powder, benzoguanamine resin powder, polytetrafluoroethylene powder, and cellulose powder; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ocher; inorganic black pigments such as black iron oxide and low oxides of titanium; inorganic purple pigments such as manganese violet and cobalt violet; inorganic green pigments such as chromium oxide, chromium hydroxide, and cobalt titanate; inorganic blue pigments such as ultramarine blue and Berlin blue; pearl pigments such as bismuth oxychloride, fish scale flakes, titanated mica, iron oxide-coated titanated mica, lower titanium oxide-coated titanated mica, photochromic titanated mica, pigments which have talc, glass, synthetic fluorphlogopite, silica, or bismuth oxychloride instead of mica in titanated mica as substrate, pigments which are coated by lower titanium oxide, colored titanium oxide, iron oxide, alumina, silica, zirconia, zinc oxide, cobalt oxide, or aluminum instead of titanium oxide in titanated mica as coating material, functional pearl pigments such as a pearl pigment having the surface coated with resin particles (Japanese Unexamined Patent Publication No. H11-92688), a pearl pigment having the surface coated with aluminum hydroxide particles (Japanese Unexamined Patent Publication No. 2002-146238), a pearl pigment having the surface coated with zinc oxide particles (Japanese Unexamined Patent Publication No. 2003-261421), and a pearl pigment having the surface coated with barium sulfate particles (Japanese Unexamined Patent Publication No. 2003-61229); metal powder pigments such as aluminum powder and copper powder; organic pigments such as zirconium, barium or aluminum rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3, and blue 1); and natural colors such as chlorophyll and 6-carotene. The above-described powder components can be used alone or by mixing two or more.

As the powder component, a surface-untreated component may be used, or a surface-treated component with silicone or fluorine compounds, silane coupling agents, Teflon (registered trademark), fatty acids, fatty acid soap, lauroyl lysine, etc. may be used. The powder components can be used alone or in combination of two or more.

In the powder cosmetic obtained by the production method of the present invention, the blending quantity of the powder component is preferably 65 to 97 mass %, and more preferably 80 to 93 mass %. If the blending quantity of the powder component is less than 65 mass %, it is difficult to obtain fully satisfactory powder cosmetics in terms of the extensibility on the skin, long-lasting property, etc. On the other hand, if the blending quantity exceeds 97 mass %, it is difficult to obtain fully satisfactory powder cosmetics in terms of the practical characteristics such as adhesion to the skin and moist feeling and in terms of the impact resistance.

In the production method of the present invention, it is preferable to contain fluorine compound-treated powder as a powder component. The homogenization of the fluorine compound-treated powder and the oil component is difficult because of the oil-repellent property of the fluorine compound, and there has been an issue in that the powder agglomeration easily takes place. According to the production method of the present invention, however, the oil component can be uniformly coated on the surface of powder particles with the use of a facing rotor type mixing apparatus with a specific structure even when such a fluorine compound-treated powder is used. Thus, the water-repellent and oil-repellent properties, which fluorine compounds have, are fully exerted, and the powder cosmetics excellent in long-lasting property can be obtained.

Examples of fluorine compounds, which are used for the treatment of the powder surface, include perfluoroalkyl phosphoric acid ester/diethanolamine salts, perfluoroalkylsilane, perfluoroalkylethyl acrylate, etc.; and compounds having a perfluoropolyether group such as perfluoropolyether dialkyl phosphoric acid and its salts, perfluoropolyethers dialkyl sulfuric acid and its salts, and perfluoropolyether dialkyl carboxylic acid and its salts.

Examples of fluorine compounds include 1H,1H,2H,2H-perfluorooctyltriethoxysilane (chemical formula (I)).

(Chemical Formula I)

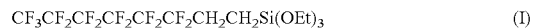

$$CF_3CF_2CF_2CF_2CF_2CF_2CH_2CH_2Si(OEt)_3 \qquad (I)$$

On the other hand, the treatment with a fluorine compound in combination with other hydrophobizing agents may be carried out. Fluorine compound-treated powders of the present invention also include powders treated with a fluorine compound in combination with other treatment agents. Specific examples include the compounds represented by chemical formula (II), which are acryl silicone compounds.

(Chemical formula II)

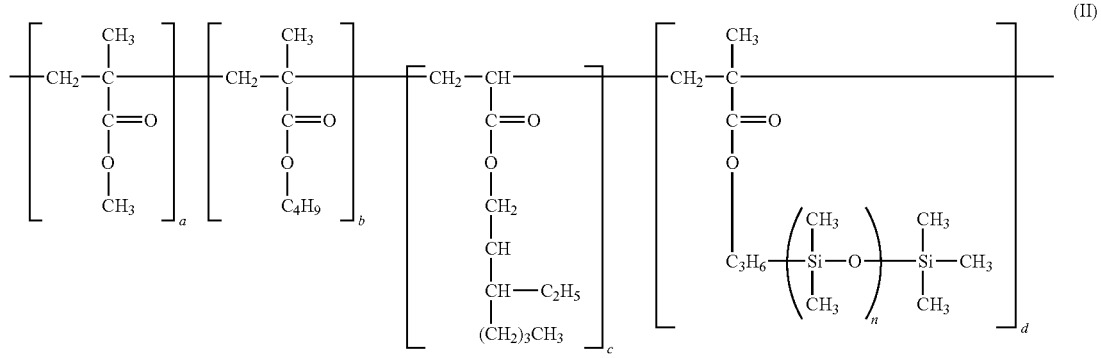

(In the formula, n is an integer, a, b, c, and d are respective molar fractions in the copolymer and non-zero, and d is 40 mol % or higher and 60 mol % or lower.)

In the powder cosmetic obtained by the production method of the present invention, the blending quantity of fluorine compound-treated powder is preferably 5 to 75 mass % with respect to the total amount of powder cosmetic. If the blending quantity of fluorine compound-treated powder is less than 5 mass %, it is difficult to actually feel the improvement effect of the long-lasting property, which is characteristic of fluorine compound-treated powder. If the blending quantity exceeds 75 mass %, the adhesion to the skin tends to be somewhat poor.

Furthermore, in the production method of the present invention, it is preferable to contain elastic powder as a powder component. It is difficult to homogenize, for example, the spherical elastic powder of silicone, polyurethane, etc. with the oil component; therefore there has been an issue in that the impact resistance, in particular, becomes worse. On the other hand, according to the production method of the present invention, it is possible to uniformly coat the surface of elastic powder particles with the oil component, with the use of a facing rotor type mixing apparatus with a specific structure, even when such an elastic powder is used. Thus, the powder cosmetic excellent in the feeling in use such as extensibility and the impact resistance can be obtained. Examples of elastic powders used in the present invention include silicone rubber powder, silicone resin powder, silicone resin coated silicone rubber powder, and polyurethane powder.

The shape of the elastic powder is preferably spherical. The average particle size is preferably 1 to 40 μm, and more preferably 3-30 μm.

Examples of commercial products include (vinyl dimethicone/methicone silsesquioxane) crosspolymer (product name: KSP-100, manufactured by Shin-Etsu Chemical Co., Ltd.), (diphenyl dimethicone/vinyl diphenyl dimethicone/silsesquioxane) crosspolymer (product name: KSP-300, manufactured by Shin-Etsu Chemical Co., Ltd.), (dimethicone/vinyl dimethicone) crosspolymer (product name: Trefil E-506, manufactured by Dow Corning Toray Co., Ltd.), hexamethylene diisocyanate/trimethylol hexyllactone crosspolymer (product name: Plastic Powder D-400, manufactured by Toshiki Pigment Co., Ltd.).

Furthermore, in the production method of the present invention, the blending quantity of elastic powder contained in the powder component is preferably 5.0 to 20.0 mass % with respect to the total amount of powder cosmetic, more preferably 8.0 to 15.0 mass %. In the conventional preparation method, the impact resistance tended to become worse when the elastic powder was blended. However, the impact resistance is excellent in the present invention even when 5% or higher elastic powder is blended, and the cosmetics having satisfactory impact resistance and being excellent in extensibility on the skin can be obtained. On the other hand, if the blending quantity exceeds 20 mass %, the impact resistance and the adhesion to the skin tend to be somewhat poor.

Oil Component

Examples of oil components used for the production method of the present invention include natural vegetable oils such as avocado oil, camellia oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japanese tung oil, jojoba oil, and germ oil; liquid oils such as triglycerin, glyceryl trioctanoate, and glyceryl triisopalmitate; animal and plant liquid oils such as cacao butter, coconut oil, horse fat, hardened coconut oil, palm oil, beef tallow, mutton tallow, hardened beef tallow, palm kernel oil, pork tallow, beef bone tallow, Japan wax kernel oil, hardened oil, heatsfoot oil, Japan wax, and hardened castor oil; waxes such as beeswax, candelilla wax, cotton wax, carnauba wax, bayberry wax, Chinese wax, spermacetim, montan wax, rice bran wax, lanolin, kapok wax, lanolin acetate, liquid lanolin, sugar cane wax, isopropyl lanolate, hexyl laurate, reduced lanolin, jojoba wax, hard lanolin, shellac wax, POE lanoline alcohol ether, POE lanoline alcohol acetate, POE cholesterol ether, lanolin fatty acid polyethylene glycol, and POE hydrogenated lanolin alcohol ether; hydrocarbon oils such as liquid paraffin, ozokerite, squalene, pristane, paraffin, ceresin, squalene, petrolatum, and microcrystalline wax; synthetic ester oils such as isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentylglycol dicaprate, diisostearyl malate, glyceryl di-2-heptylundecanoate, trimethylolpropane tri-2-ethylhexanolate, trimethylolpropane triisostearate, pentanerythritol tetra-2-ethylhexanolate, glyceryl tri(2-ethylhexanoate), trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, cetostearyl alcohol, acetoglyceride, 2-heptylundecyl palmitate, diisobutyl adipate, 2-octyldodecyl ester N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, and triethyl citrate; silicone oils such as dimethylpolysiloxane, methylphenylpolysiloxane, methyl hydrogen polysiloxane, decamethylpolysiloxane, dodecamethylpolysiloxane, and tetramethyltetrahydrogenpolysiloxane; fluororesin, and acrylic resin. The above-described oil components can be used alone or by mixing two or more.

Furthermore, in the production method of the present invention, it is preferable to contain, as an oil component, a high-viscosity oil having a viscosity of 100 to 50000 mPa·s at 25° C. The viscosity can be measured with a B-type viscometer, and they are the values that can be measured at a rotation speed of 12 rpm for a non-Newtonian fluid. In the conventional production method, it was very difficult to uniformly disperse high-viscosity oil into powder. According to the production method of the present invention, however, it is possible to uniformly coat the surface of powder particles with high-viscosity oil, with the use of a facing rotor type mixing apparatus with a specific structure. Therefore, when such a high-viscosity oil is used, the powder cosmetic excellent in the adhesion to the skin and the long-lasting property can be obtained. In addition, even when high-viscosity oil and a highly oil-repellent powder that has been treated with a fluorine compound are used at the same time, the agglomeration of the powder component does not take place, resulting in a uniform finish, and the powder cosmetics with excellent usability can be obtained.

Examples of high-viscosity oils, which are used in the production method of the present invention, include hydrogenated polyisobutene; glyceryl triisostearate; diisostearyl malate; silicone oils such as dimethylpolysiloxane and diphenyl dimethicone; castor oil; and the derivatives of dimer acids and dimer diols such as di(isostearyl/phytosteryl) dimer dilinoleate, dimer dilinoleyl diisostearate, and dimer dilinoleyl dimer dilinoleate.

In the powder cosmetics obtained by the production method of the present invention, the blending quantity of the oil component is preferably 3 to 35 mass %, and more preferably 7 to 20 mass %. If the blending quantity of the oil component is less than 3 mass %, it is difficult to obtain fully satisfactory powder cosmetic in terms of the practical characteristics such as adhesion to the skin and moist feeling and in terms of the impact resistance. On the other hand, if the blending quantity of the oil component exceeds 35 weight %, it is difficult to obtain fully satisfactory powder cosmetics in terms of the extensibility on the skin and long-lasting property.

Here, the blending quantity of high-viscosity oil used in the present invention is, from the viewpoint of the adhesion to the skin and extensibility on the skin, preferably 0.005 parts by weight or higher and 0.5 parts by weight or lower with respect to 1 part by weight of fluorine compound-treated powder, and more preferably 0.01 parts by weight or higher and 0.15 parts by weight or lower.

Facing Rotor Type Mixing Apparatus

In the production method of the present invention, the apparatus used for mixing a powder component and an oil component is a facing rotor type mixing apparatus which has a first rotor with a plurality of blades and a second rotor with a plurality of blades in a mixing chamber, in which the first rotor and the second rotor face each other and have rotating shafts on same axis line. In the facing rotor type mixing apparatus, raw materials are fed into an introduction opening on a first rotor side, the raw materials are mixed by rotating the first rotor and the second rotor in same or opposite directions to each other, and the mixed raw materials are discharged from a discharge opening in a second rotor side.

By mixing the powder component and the oil component with the use of the facing rotor type mixing apparatus with a specific structure, it is possible to uniformly coat the surface of powder particles with the oil component without the agglomeration of the powder component. Because the facing rotor type mixing apparatus used in the present invention is a dry mixing apparatus, it is not necessary to dissolve the powder component and the oil component in a suitable mixing solvent. Thus, the production process is simple compared with the wet mixing, and there are few safety issues and environmental issues.

The facing rotor type mixing apparatus used in the present invention has been used as a grinding apparatus in the past, and it has been publicly known to persons skilled in the art as a grinding device. For example, the grinding devices described in Japanese Unexamined Patent Publication No. 2002-79183, Japanese Unexamined Patent Publication No. 2003-1127, Japanese Unexamined Patent Publication No. 2003-10712, Japanese Unexamined Patent Publication No. 2003-71307, etc. can be used as the mixing apparatus of the present invention. As a commercial apparatus, for example, a cyclone mill (manufactured by Flo-Tec, Ltd.) can be listed.

A schematic drawing of one example of the facing rotor type mixing apparatus that was used in the production method of the present invention is shown in FIG. 1. However, the facing rotor type mixing apparatus used in the present invention is not limited by this example.

In the facing rotor type mixing apparatus 10, a first rotor 14 and a second rotor 15, which are driven by respective rotating motors 12 and 13, are installed inside the mixing chamber 11 so as to face each other on the same axis line. A raw material introduction opening 16 is communicated with the mixing chamber 11 on the first rotor 14 side, and a discharge opening 17 is communicated with the mixing chamber 11 on the second rotor 15 side. In addition, a raw material supplying device 20 is installed above the introduction opening 16 of the facing rotor type mixing apparatus 10, and a collecting device 30 (and a collection container 32) and a suction device 40 are connected to the end of the discharge opening 17.

In the facing rotor type mixing apparatus 10, the first rotor 14 and the second rotor 15, disposed so as to face each other on the same axis line, rotate integrally with the rotating shafts of the motors 12 and 13. In the facing rotor type mixing apparatus 10, the first rotor 14 and the second rotor 15 are rotated at a fast speed, in the same or opposite directions to each other, by the motors 12 and 13. In the state of fast rotation, a target mixture of raw materials is loaded through the raw material introduction opening 16 with the raw material supplying device 20. The mixture of raw materials loaded into the facing rotor type mixing apparatus 10 vigorously collides with the first rotor 14, second rotor 15, or the inner wall surface of the mixing chamber 11. In addition, the raw material components collide with each other and are uniformly mixed and dispersed. As a result, a mixture in which the surface of powder particles is uniformly coated with the oil component is obtained without the agglomeration of powder components.

The facing first rotor 14 and second rotor 15 are rotated in the same or opposite directions to each other. In the production method of the present invention, it is preferable to rotate the first rotor and the second rotor in the opposite directions. A larger shear stress can be generated by the rotation in the opposite directions to each other than the rotation in the same direction. Thus, the agglomeration of powder components is difficult to take place, and a homogeneous mixture can be easily obtained. The speed of rotation of the first rotor 14 and the speed of the second rotor 15 can be suitably adjusted, for example, at 1000 to 10000 rpm, and preferably 3000 to 8000 rpm.

In the first rotor 14 and the second rotor 15, a plurality of blades are radially installed around the boss installed on the rotating shaft of the motors 12 and 13, respectively. The number of blades per rotor is normally 2 to 16. In the first rotor 14 and the second rotor 15, the shape of the rotors and the number of blades can be either the same or different from each other.

The target mixture blended in the mixing chamber 11 is discharged from the discharge opening 17. To the end of the discharge opening 17, a collecting device 30 and a suction device 40 are connected. By the operation of the suction device 40, the target mixture is continuously discharged from the opening 17. The discharged target mixture is collected with the collecting device 30 into the collection container 32. The operational conditions of the suction device 40 can be suitably adjusted depending upon the kind and quantity of the target mixture and the rotation speed of rotors. In addition, a mixture can be continuously produced by continuously loading a mixture of raw materials with the raw material supplying device 20 while the suction device 40 and the collecting device 30 are being operated.

The powder component and the oil component may be loaded individually or simultaneously into the facing rotor type mixing apparatus 10. However, it is normally preferable to carry out preliminary mixing with a simple agitation apparatus such as a Henschel mixer or a Nauta mixer. If they are loaded, without preliminary mixing, into the facing rotor type mixing apparatus 10, only light powder components are discharged at the forefront without being sufficiently mixed with the oil component. Thus, the control of mixing process will become difficult.

In the production method of the present invention, when a powdery solid cosmetic such as foundation is produced, the obtained above-described mixture of the powder component and the oil component is normally filled into, for example, a metal or plastic inner tray, and the solidification by dry molding is carried out. As a solidification method, prior publicly known press molding etc. can be used.

In the powder cosmetic made by the production method of the present invention, other components generally used in skin external preparations such as cosmetics or pharmaceuticals can be appropriately blended, as necessary, so far as the effect of the present invention is not undermined. Examples of the other components include anionic surfactants, cationic surfactants, amphoteric surfactants, nonionic surfactants, moisturizers, water-soluble polymers, thickeners, film-forming agents, UV absorbers, metal ion sequestering agents, lower alcohols, polyhydric alcohols, saccharides, amino acids, organic amines, polymer emulsions, pH adjusters, skin nutrients, vitamins, antioxidants, antioxidant promoters, perfume, and water. The powder cosmetic of the present invention can be produced by normal preparation methods depending on a desired product form.

The production method according to the present invention is preferably utilized in powder cosmetics in the powder or solid form, such as foundation, eyeshadow, cheek color, body powder, perfume powder, baby powder, pressed powder, deodorant powder, and face powder.

EXAMPLE

Hereinafter, the present invention will be described in further detail by examples. However, the present invention is not limited by these examples. The blending quantity is expressed in mass % unless otherwise noted.

Initially, the evaluation methods used in the present examples will be explained.

<Evaluation of Practical Characteristics>

Powder cosmetics obtained in each example and the comparative example were evaluated by 20 female panelists. The feeling of particulate fineness of powder was evaluated by touching with a finger. Then, respective cosmetics were applied on each half of the face, and the moist feeling and smoothness, powdery texture, uniform finish, and the long-lasting property after 3 hours were compared and evaluated, respectively.

| | |
|---|---|
| 17 or more panelists answered that the powder cosmetic was good | ⊚ |
| 12 to 16 panelists answered that the powder cosmetic was good | ○ |
| 9 to 11 panelists answered that the powder cosmetic was good | Δ |
| 5 to 8 panelists answered that the powder cosmetic was good | X |
| 4 or less panelists answered that the powder cosmetic was good | XX |

<Evaluation of Impact Resistance>

Powder cosmetics obtained in each examples and the comparative examples were press-molded into plastic to obtain the samples that were set in cosmetic compact containers. A sample was dropped, from a height of 30 cm in a horizontal state, onto an iron plate with a thickness of 20 mm. The number of droppings until the breakage takes place was regarded as the evaluation of the impact resistance.

The present inventors have produced powder cosmetics (foundation) of Example 1 and Comparative Example 1 by using the formulations shown in the following Table 1. Then, the practical characteristics and the impact resistance of the obtained various powder cosmetics were evaluated according to the above-described evaluation criteria.

In the powder cosmetic of Example 1, the oil component is added to the powder component of the formulation and mixed with a Henschel mixer (manufactured by Mitsui Miike Engineering Corporation) for a fixed amount of time, and then they were mixed two times with the facing rotor type mixing apparatus (cyclone mill: manufactured by FLO-TEC, Ltd.) shown in FIG. 1 and press-molded into a plastic inner tray. On the other hand, in the powder cosmetic of Comparative Example 1, the oil component is added to the powder component of the same formulation as that of Example 1 and mixed with a Henschel mixer, and then they were mixed two times with the pulverizer (manufactured by Hosokawa Micron Corporation), which is a hammer mill, and press-molded into a plastic inner tray.

TABLE 1

| Foundation | Example 1 | Comparative Example 1 |
|---|---|---|
| Sericite | 10 | 10 |
| Synthetic mica | 10 | 10 |
| Talc | Balance | Balance |
| Titanium oxide | 11 | 11 |
| Red interference pearl pigment | 2 | 2 |
| Zinc oxide | 2 | 2 |
| Red iron oxide | 0.8 | 0.8 |
| Yellow iron oxide | 2 | 2 |
| Black iron oxide | 0.1 | 0.1 |
| Spherical silicone elastic powder[*1] | 6 | 6 |
| Spherical nylon powder | 4 | 4 |
| Dimethylpolysiloxane (5 mPa · s) | 3 | 3 |
| Dimethylpolysiloxane (5000 mPa · s) | 2 | 2 |
| Squalane | 3 | 3 |
| Petrolatum | 2 | 2 |
| Sorbitan sesquiisostearate | 1 | 1 |
| Paraben | Q.S. | Q.S. |
| Antioxidant | Q.S. | Q.S. |
| Perfume | Q.S. | Q.S. |
| Production method | Premix with Henschel mixer ↓ Mix two times with facing rotor type mixing apparatus ↓ Press-mold into plastic inner tray | Premix with Henschel mixer ↓ Mix two times with pulverizer ↓ Press-mold into plastic inner tray |
| Feeling of particulate fineness | ⊚ | Δ |
| Moist feeling | ○ | Δ |
| Smoothness | ⊚ | ○ |
| Powdery texture | ⊚ | Δ |
| Uniform finish | ⊚ | Δ |
| Long-lasting property | ○ | Δ |

TABLE 1-continued

| Foundation | Example 1 | Comparative Example 1 |
|---|---|---|
| Impact resistance times | 12 times | 5 times |

*[1](Vinyl dimethicone/Methicone silsesquioxane) crosspolymer (KSP-100: manufactured by Shin-Etsu Chemical Co., Ltd.) 2.0% (Diphenyl dimethicone/Vinyl diphenyl dimethicone/Silsesquioxane) crosspolymer (KSP-300: manufactured by Shin-Etsu Chemical Co., Ltd.) 2.0% (Dimethicone/Vinyl dimethicone) crosspolymer (Trefil E-506: manufactured by Dow Corning Toray Co., Ltd.) 2.0%

As shown in the above Table 1, the powder cosmetic of Example 1, in which a facing rotor type mixing apparatus was used, was excellent in various practical characteristics such as the feeling of particulate fineness, moist feeling, smoothness, powdery texture, uniform finish, and long-lasting property, and the impact resistance was also good.

On the other hand, the powder cosmetic of Comparative Example 1, in which a pulverizer (hammer mill) was used, was somewhat good in smoothness; however, the excellent evaluation could not be obtained in other practical characteristics. In addition, the evaluation in impact resistance was a half or lower of that of Example 1.

Subsequently, various evaluations were carried out, similarly to the above Table 1, by using various powder cosmetic formulations shown in the following Tables 2 to 5. The production methods of various powder cosmetics are the same as those of Example 1 and Comparative Example 1. The evaluation results are shown together in Tables 2 to 5.

TABLE 2

| Foundation | Example 2 | Comparative Example 2 |
|---|---|---|
| Silicone-treated sericite | 12 | 12 |
| Silicone-treated mica | Balance | Balance |
| Silicone-treated talc | 23 | 23 |
| Silicone-treated titanium oxide | 12 | 12 |
| Aluminum stearate-treated fine titanium oxide | 4 | 4 |
| Silicone-treated red iron oxide | 1.2 | 1.2 |
| Silicone-treated yellow iron oxide | 2.5 | 2.5 |
| Silicone-treated black iron oxide | 0.9 | 0.9 |
| Polyurethane powder | 5 | 5 |
| Fine zinc oxide | 2 | 2 |
| Parabene | Q.S. | Q.S. |
| Dimethylpolysiloxane (5 mPa · s) | 3 | 3 |
| Hydrogenated isopolybutene (20000 mPa · s) | 2 | 2 |
| Methylphenylpolysiloxane | 3 | 3 |
| Octyl methoxycinnamate | 3 | 3 |
| Polyether silicone | 1 | 1 |
| Antioxidant | Q.S. | Q.S. |
| Perfume | Q.S. | Q.S. |
| Production method | Premix with Henschel mixer ↓ Mix two times with facing rotor type mixing apparatus ↓ Press-mold into plastic inner tray | Premix with Henschel mixer ↓ Mix two times with pulverizer ↓ Press-mold into plastic inner tray |
| Feeling of particulate fineness | ⊚ | X |
| Moist feeling | ○ | Δ |
| Smoothness | ⊚ | ○ |
| Powdery texture | ○ | X |
| Uniform finish | ⊚ | Δ |
| Long-lasting property | ○ | Δ |
| Impact resistance | 10 times | 4 times |

TABLE 3

| Foundation | Example 3 | Comparative Example 3 |
|---|---|---|
| Silicone-treated sericite | 12 | 12 |
| Silicone-treated mica | Balance | Balance |
| Silicone-treated talc | 23 | 23 |
| Silicone-treated titanium oxide | 12 | 12 |
| Aluminum stearate-treated fine titanium oxide | 4 | 4 |
| Silicone-treated red iron oxide | 1.2 | 1.2 |
| Silicone-treated yellow iron oxide | 2.5 | 2.5 |
| Silicone-treated black iron oxide | 0.9 | 0.9 |
| Polyurethane powder | 5 | 5 |

TABLE 3-continued

| Foundation | Example 3 | Comparative Example 3 |
|---|---|---|
| Fine zinc oxide | 2 | 2 |
| Chlorphenesin | Q.S. | Q.S. |
| Dimethylpolysiloxane (1000 mPa · s) | 3 | 3 |
| Glyceryl triisostearate (6000 mPa · s) | 2 | 2 |
| Methylphenylpolysiloxane | 3 | 3 |
| Octyl methoxycinnamate | 3 | 3 |
| Polyether silicone | 1 | 1 |
| Antioxidant | Q.S. | Q.S. |
| Perfume | Q.S. | Q.S. |
| Production method | Premix with Henschel mixer ↓ Mix two times with facing rotor type mixing apparatus ↓ Press-mold into plastic inner tray | Premix with Henschel mixer ↓ Mix two times with pulverizer ↓ Press-mold into plastic inner tray |
| Feeling of particulate fineness | ⊚ | XX |
| Moist feeling | ⊚ | ○ |
| Smoothness | ⊚ | ○ |
| Powdery texture | ○ | Δ |
| Uniform finish | ⊚ | ○ |
| Long-lasting property | ○ | X |
| Impact resistance | 10 times | 6 times |

TABLE 4

| Foundation | Example 4 | Comparative Example 4 |
|---|---|---|
| Fluorine acryl-treated sericite | 10 | 10 |
| Fluorine acryl-treated mica | Balance | Balance |
| Fluorine acryl-talc | 28 | 28 |
| Fluorine-treated titanium oxide | 12 | 12 |
| Aluminum stearate-treated fine titanium oxide | 4 | 4 |
| Fluorine-treated red iron oxide | 1.2 | 1.2 |
| Fluorine-treated yellow iron oxide | 2.5 | 2.5 |
| Fluorine-treated black iron oxide | 0.9 | 0.9 |
| Silicone elastic powder*[2] | 6 | 6 |
| Spherical polyethylene powder | 3 | 3 |
| Blue interference pearl pigment | 3 | 3 |
| Fine zinc oxide | 7 | 7 |
| Fine silica | 1 | 1 |
| Parabene | Q.S. | Q.S. |
| Dimethylpolysiloxane (100 mPa · s) | 3 | 3 |
| Dimethylpolysiloxane (5000 mPa · s) | 3 | 3 |
| Methylphenylpolysiloxane | 2 | 2 |
| Octyl methoxycinnamate | 3 | 3 |
| Polyether silicone | 1 | 1 |
| Antioxidant | Q.S. | Q.S. |
| Perfume | Q.S. | Q.S. |
| Production method | Premix with Henschel mixer ↓ Mix two times with facing rotor type mixing apparatus ↓ Press-mold into plastic inner tray | Premix with Henschel mixer ↓ Mix two times with pulverizer ↓ Press-mold into plastic inner tray |
| Feeling of particulate fineness | ⊚ | ○ |
| Moist feeling | ○ | Δ |
| Smoothness | ⊚ | ○ |
| Powdery texture | ○ | Δ |
| Uniform finish | ⊚ | Δ |
| Long-lasting property | ⊚ | Δ |
| Impact resistance | 13 times | 5 times |

*[2](Vinyl dimethicone/Methicone silsesquioxane) crosspolymer (KSP-100: manufactured by Shin-Etsu Chemical Co., Ltd.) 2.0% (Diphenyl dimethicone/Vinyl diphenyl dimethicone/Silsesquioxane) crosspolymer (KSP-300: manufactured by Shin-Etsu Chemical Co., Ltd.) 4.0%

TABLE 5

| White powder (Pressed powder) | Example 5 | Comparative Example 5 |
|---|---|---|
| Metal soap-treated talc | Balance | Balance |
| Synthetic mica | 15 | 15 |
| Zinc oxide | 5 | 5 |
| Red interference pearl pigment | 3 | 3 |
| Fine titanium oxide | 3 | 3 |
| Spherical silicone elastic powder[*3] | 10 | 10 |
| Dimethylpolysiloxane (5000 mPa · s) | 2 | 2 |
| Diisostearyl malate (2000 mPa · s) | 1 | 1 |
| Squalane | 2 | 2 |
| Ester oil | 2 | 2 |
| Parabene | Q.S. | Q.S. |
| Antioxidant | Q.S. | Q.S. |
| Perfume | Q.S. | Q.S. |
| Production method | Premix with Henschel mixer ↓ Mix two times with facing rotor type mixing apparatus ↓ Press-mold into plastic inner tray | Premix with Henschel mixer ↓ Mix two times with pulverizer ↓ Press-mold into plastic inner tray |
| Feeling of particulate fineness | ⊚ | Δ |
| Moist feeling | Δ | X |
| Smoothness | ⊚ | ○ |
| Powdery texture | ○ | Δ |
| Uniform finish | ⊚ | Δ |
| Long-lasting property | ○ | Δ |
| Impact resistance | 11 times | 4 times |

[*3] (Vinyl dimethicone/Methicone silsesquioxane) crosspolymer (KSP-100: manufactured by Shin-Etsu Chemical Co., Ltd.)

As shown in the above Tables 2 to 5, the powder cosmetics of Examples 2 to 5, in which a facing rotor type mixing apparatus was used, were excellent in various practical characteristics such as the feeling of particulate fineness, moist feeling, smoothness, powdery texture, and uniform finish, compared with the powder cosmetics of Comparative Examples 2 to 5, in which a pulverizer was used. In addition, the impact resistance was also good.

TABLE 6

| Foundation | Example 6 | Comparative Example 6 |
|---|---|---|
| 1H,1H,2H,2H-perfluorooctyltriethoxysilane (5%)-treated sericite | 10 | 10 |
| 1H,1H,2H,2H-perfluorooctyltriethoxysilane (5%)-treated mica | 15 | 15 |
| 1H,1H,2H,2H-perfluorooctyltriethoxysilane (5%)-treated talc | Balance | Balance |
| Barium Sulfate | 15 | 15 |
| Titanium oxide | 15 | 15 |
| Red interference pearl pigment | 2 | 2 |
| Zinc oxide | 2 | 2 |
| Red iron oxide | 0.8 | 0.8 |
| Yellow iron oxide | 2 | 2 |
| Black iron oxide | 0.1 | 0.1 |
| Spherical silicone elastic powder[*1] | 6 | 6 |
| Spherical nylon powder | 4 | 4 |
| Silica silylate | 2 | 2 |
| Dimethylpolysiloxane (5 mPa · s) | 3 | 3 |
| Dimethylpolysiloxane (5000 mPa · s) | 2 | 2 |
| Squalane | 3 | 3 |
| Petrolatum | 2 | 2 |
| Sorbitan sesquiisostearate | 1 | 1 |
| Chlorphenesin | Q.S. | Q.S. |
| Antioxidant | Q.S. | Q.S. |
| Perfume | Q.S. | Q.S. |
| Production method | Premix with Henschel mixer ↓ Mix two times with facing rotor type mixing apparatus ↓ Press-mold into plastic inner tray | Premix with Henschel mixer ↓ Mix two times with pulverizer ↓ Press-mold into plastic inner tray |

TABLE 6-continued

| Foundation | Example 6 | Comparative Example 6 |
|---|---|---|
| Feeling of particulate fineness | ⊚ | Δ |
| Moist feeling | ○ | Δ |
| Smoothness | ⊚ | ○ |
| Powdery texture | ⊚ | Δ |
| Uniform finish | ⊚ | X |
| Long-lasting property | ⊚ | ○ |
| Impact resistance | 13 times | 6 times |

*[1](Vinyl dimethicone/Methicone silsesquioxane) crosspolymer (KSP-100: manufactured by Shin-Etsu Chemical Co., Ltd.) 2.0% (Diphenyl dimethicone/Vinyl diphenyl dimethicone/Silsesquioxane) crosspolymer (KSP-300: manufactured by Shin-Etsu Chemical Co., Ltd.) 2.0%

As shown in the above Table 6, a powder cosmetic of Example 6, in which a facing rotor type mixing apparatus was used, was excellent in various practical characteristics such as the feeling of particulate fineness, moist feeling, smoothness, powdery texture, uniform finish, and long-lasting property, and the impact resistance was also good though the fluorine-treated powder, 1H,1H,2H,2H-perfluorooctyltriethoxysilane (chemical formula (I)), and the high-viscosity oil, dimethylpolysiloxane (5000 mPa·s), were used in combination.

On the other hand, the powder cosmetic of Comparative Example 6, in which a pulverizer (hammer mill) was used, was somewhat good in smoothness; however, the excellent evaluation could not be obtained in other practical characteristics. In addition, the evaluation in impact resistance was a half or lower of that of Example 6.

The above-described chemical formula (I) is represented by the following formula.

(Chemical Formula I)

$$CF_3CF_2CF_2CF_2CF_2CF_2CH_2CH_2Si(OEt)_3 \quad (I)$$

Subsequently, various evaluations were carried out, similarly to the above Table 6, by using various powder cosmetic formulations shown in the following Tables 7 to 10. The production methods of various powder cosmetics are the same as those of Example 6 and Comparative Example 6. The evaluation results are shown together in Tables 7 to 10.

TABLE 7

| Foundation | Example 7 | Comparative Example 7 |
|---|---|---|
| 1H,1H,2H,2H-perfluorooctyltriethoxysilane (5%)-treated sericite | 9 | 9 |
| 1H,1H,2H,2H-perfluorooctyltriethoxysilane (5%)-treated mica | Balance | Balance |
| 1H,1H,2H,2H-perfluorooctyltriethoxysilane (5%)-treated talc | 28 | 28 |
| Boron nitride | 5 | 5 |
| Silicone-treated titanium oxide | 10 | 10 |
| Aluminum stearate-treated fine titanium oxide | 4 | 4 |
| Silicone-treated red iron oxide | 1.2 | 1.2 |
| Silicone-treated yellow iron oxide | 2.6 | 2.6 |
| Silicone-treated black iron oxide | 0.4 | 0.4 |
| Polyurethane powder | 10 | 10 |
| Fine zinc oxide | 1 | 1 |
| Silica silylate | 2 | 2 |
| Parabene | Q.S. | Q.S. |
| Dimethylpolysiloxane (5 mPa · s) | 3 | 3 |
| Hydrogenated isopolybutene (20000 mPa · s) | 2 | 2 |
| Methylphenylpolysiloxane | 2.5 | 2.5 |
| Octyl methoxycinnamate | 3 | 3 |
| Octocrylene | 1 | 1 |
| Sorbitan sesquiisostearate | 0.5 | 0.5 |
| Antioxidant | Q.S. | Q.S. |
| Perfume | Q.S. | Q.S. |
| Production method | Premix with Henschel mixer ↓ Mix two times with facing rotor type mixing apparatus ↓ Press mold into plastic inner tray | Premix with Henschel mixer ↓ Mix two times with pulverizer ↓ Press-mold into plastic inner tray |
| Feeling of particulate fineness | ⊚ | Δ |
| Moist feeling | ○ | Δ |
| Smoothness | ⊚ | ○ |
| Powdery texture | ○ | Δ |
| Uniform finish | ⊚ | Δ |
| Long-lasting property | ○ | Δ |
| Impact resistance | 10 times | 4 times |

TABLE 8

| Foundation | Example 8 | Comparative Example 8 |
|---|---|---|
| 1H,1H,2H,2H-perfluorooctyltriethoxysilane (5%)/Formula(II) copolymer (2%)-treated sericite | 12 | 12 |
| 1H,1H,2H,2H-perfluorooctyltriethoxysilane (5%)/Formula(II) copolymer (2%)-treated mica | Balance | Balance |
| 1H,1H,2H,2H-perfluorooctyltriethoxysilane (5%)/Formula(II) copolymer (2%)-treated talc | 23 | 23 |
| Synthetic mica | 16 | 16 |
| Silicone-treated titanium oxide | 8 | 8 |
| Aluminum stearate-treated fine titanium oxide | 4 | 4 |
| Silicone-treated red iron oxide | 1.2 | 1.2 |
| Silicone-treated yellow iron oxide | 2.5 | 2.5 |
| Silicone-treated black iron oxide | 0.9 | 0.9 |
| Polyurethane powder | 5 | 5 |
| Fine zinc oxide | 2 | 2 |
| Chlorphenesin | Q.S. | Q.S. |
| Dimethylpolysiloxane (1000 mPa · s) | 3 | 3 |
| Glyceryl triisostearate (6000 mPa · s) | 2 | 2 |
| Methylphenylpolysiloxane | 3 | 3 |
| Octyl methoxycinnamate | 2 | 2 |
| Octocrylene | 1 | 1 |
| Polyether silicone | 1 | 1 |
| Antioxidant | Q.S. | Q.S. |
| Perfume | Q.S. | Q.S. |
| Production method | Premix with Henschel mixer ↓ Mix two times with facing rotor type mixing apparatus ↓ Press-mold into plastic inner tray | Premix with Henschel mixer ↓ Mix two times with pulverizer ↓ Press-mold into plastic inner tray |
| Feeling of particulate fineness | ⊚ | X |
| Moist feeling | ⊚ | ○ |
| Smoothness | ⊚ | X |
| Powdery texture | ○ | Δ |
| Uniform finish | ⊚ | ○ |
| Long-lasting property | ⊚ | ○ |
| Impact resistance | 16 times | 8 times |

Chemical formula (II) described in Table 8 is represented by the following formula.

(Chemical formula II)

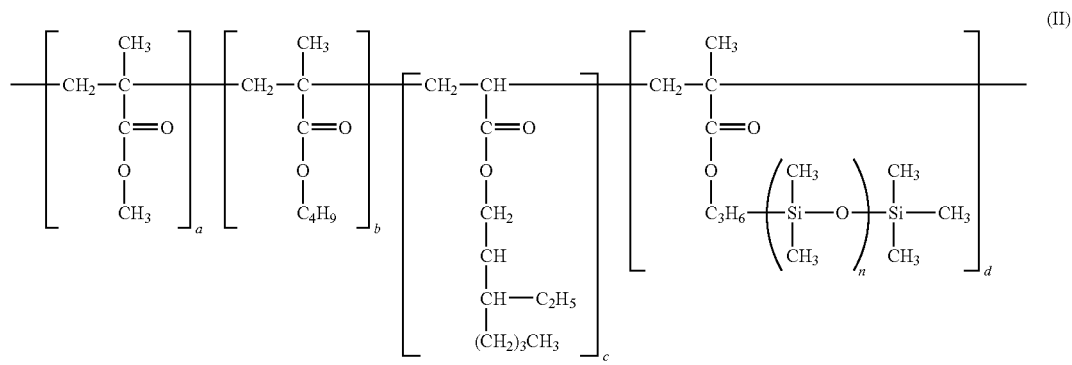

(In the formula, n is an integer, a, b, c, and d are respective molar fractions in the copolymer and non-zero, and d is 40 mol % or higher and 60 mol % or lower.)

TABLE 9

| Foundation | Example 9 | Comparative Example 9 |
|---|---|---|
| 1H,1H,2H,2H-perfluorooctyltriethoxysilane (5%)/Formula(II) copolymer (2%)-treated sericite | 10 | 10 |

TABLE 9-continued

| Foundation | Example 9 | Comparative Example 9 |
|---|---|---|
| 1H,1H,2H,2H-perfluorooctyltriethoxysilane (5%)/Formula(II) copolymer (2%)-treated mica | Balance | Balance |
| 1H,1H,2H,2H-perfluorooctyltriethoxysilane (5%)/Formula(II) copolymer (2%)-treated talc | 28 | 28 |
| 1H,1H,2H,2H-perfluorooctyltriethoxysilane (3%)-treated titanium | 12 | 12 |
| Aluminum stearate-treated fine titanium oxide | 4 | 4 |
| 1H,1H,2H,2H-perfluorooctyltriethoxysilane (3%)-treated red iron oxide | 1.2 | 1.2 |
| 1H,1H,2H,2H-perfluorooctyltriethoxysilane (3%)-treated yellow iron oxide | 2.5 | 2.5 |
| 1H,1H,2H,2H-perfluorooctyltriethoxysilane (3%)-treated black iron oxide | 0.9 | 0.9 |
| Silicone elastic powder*[2] | 6 | 6 |
| Spherical polyethylene powder | 3 | 3 |
| Blue interference pearl pigment | 3 | 3 |
| Fine zinc oxide | 7 | 7 |
| Fine silica | 1 | 1 |
| Parabene | Q.S. | Q.S. |
| Dimethylpolysiloxane (100 mPa · s) | 3 | 3 |
| Dimethylpolysiloxane (5000 mPa · s) | 3 | 3 |
| Methylphenylpolysiloxane | 2 | 2 |
| Octyl methoxycinnamate | 3 | 3 |
| Polyether silicone | 1 | 1 |
| Antioxidant | Q.S. | Q.S. |
| Perfume | Q.S. | Q.S. |
| Production method | Premix with Henschel mixer ↓ Mix two times with facing rotor type mixing apparatus ↓ Press-mold into plastic inner tray | Premix with Henschel mixer ↓ Mix two times with pulverizer ↓ Press-mold into plastic inner tray |
| Feeling of particulate fineness | ⊚ | ○ |
| Moist feeling | ○ | Δ |
| Smoothness | ⊚ | ○ |
| Powdery texture | ○ | Δ |
| Uniform finish | ⊚ | Δ |
| Long-lasting property | ⊚ | Δ |
| Impact resistance | 13 times | 5 times |

*[2](Vinyl dimethicone/Methicone silsesquioxane) crosspolymer (KSP-100: manufactured by Shin-Etsu Chemical Co., Ltd.) 2.0% (Diphenyl dimethicone/Vinyl diphenyl dimethicone/Silsesquioxane) crosspolymer (KSP-300: manufactured by Shin-Etsu Chemical Co., Ltd.) 4.0%

TABLE 10

| White powder (Pressed powder) | Example 10 | Comparative Example 10 |
|---|---|---|
| Metal soap-treated talc | Balance | Balance |
| Synthetic mica | 15 | 15 |
| Zinc oxide | 5 | 5 |
| Red interference pearl pigment | 3 | 3 |
| Fine titanium oxide | 3 | 3 |
| Spherical silicone elastic powder*[3] | 10 | 10 |
| 1H,1H,2H,2H-perfluorooctyltriethoxysilane (5%)/Formula(II) copolymer (2%)-treated talc | 25 | 25 |
| Dimethylpolysiloxane (5000 mPa · s) | 2 | 2 |
| Diisostearyl malate (2000 mPa · s) | 1 | 1 |
| Squalane | 2 | 2 |
| Ester oil | 2 | 2 |
| Chlorphenesin | Q.S. | Q.S. |
| Antioxidant | Q.S. | Q.S. |
| Perfume | Q.S. | Q.S. |
| Production method | Premix with Henschel mixer ↓ Mix two times with facing rotor type mixing apparatus ↓ Press-mold into plastic inner tray | Premix with Henschel mixer ↓ Mix two times with pulverizer ↓ Press-mold into plastic inner tray |

TABLE 10-continued

| White powder (Pressed powder) | Example 10 | Comparative Example 10 |
|---|---|---|
| Feeling of particulate fineness | ⊚ | Δ |
| Moist feeling | ○ | ○ |
| Smoothness | ⊚ | ○ |
| Powdery texture | ○ | Δ |
| Uniform finish | ⊚ | Δ |
| Long-lasting property | ⊚ | ○ |
| Impact resistance | 11 times | 4 times |

*[3](Vinyl dimethicone/Methicone silsesquioxane) crosspolymer (KSP-100: manufactured by Shin-Etsu Chemical Co., Ltd.)

As shown in the above Tables 7 to 10, the powder cosmetics of Examples 7 to 10, in which a facing rotor type mixing apparatus was used, were excellent in various practical characteristics such as the feeling of particulate fineness, moist feeling, smoothness, powdery texture, and uniform finish, compared with the powder cosmetics of Comparative Examples 7 to 10, in which a pulverizer was used, though a fluorine-treated powder and a high-viscosity oil were used in combination. In addition, the impact resistance was also good.

Furthermore, micrographs were taken with a scanning electron microscope (VE-8800: manufactured by Keyence Co.) to know the particle state of the mixture of powder component/oil component obtained in the above Example 4 and Comparative Example 4. The micrographs are shown in FIG. 2.

Figure 2:
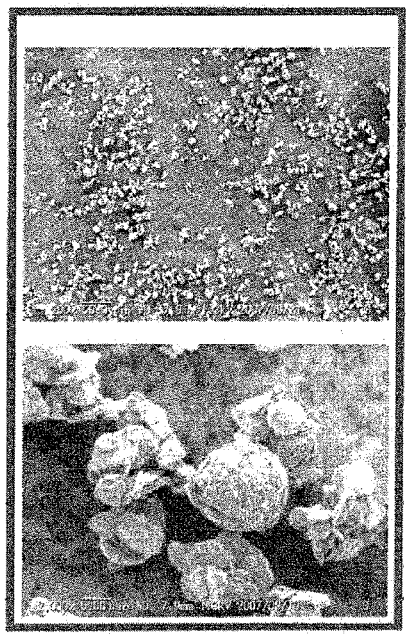
FIG. 2 shows scanning electron micrographs for the mixture of powder component/oil component obtained in Example 4 and Comparative Example 4.
Figure 2:
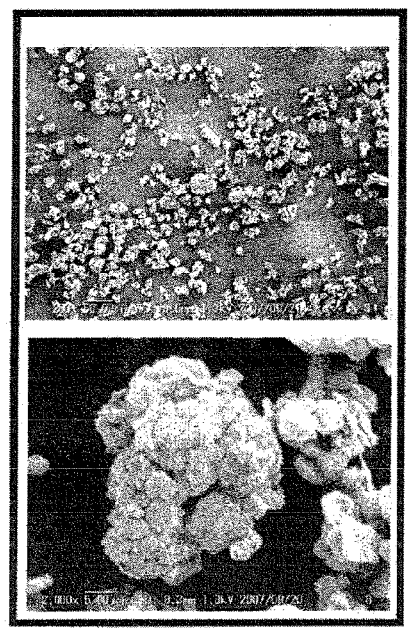

As is clear from FIG. 2, the powder surface was observed to be uniformly coated with the oil component, in the nearly primary particle state, in the mixture of Example 4, in which a facing rotor type mixing apparatus was used. On the other hand, it was found in Comparative Example 4, in which a pulverizer was used, that the particles were large compared with Example 4 and the powder components were agglomerated.

Subsequently, for the mixture of powder component/oil component obtained in the above Example 4 and Comparative Example 4, the particle size distribution was measured with a laser diffraction and scattering type particle size distribution measurement device (Microtrac MT3000II: manufactured by Nikkiso Co., Ltd.). For comparison, the same test was also carried out for the product premixed with a Henschel mixer. The results are shown in FIG. 3.

Figure 3:
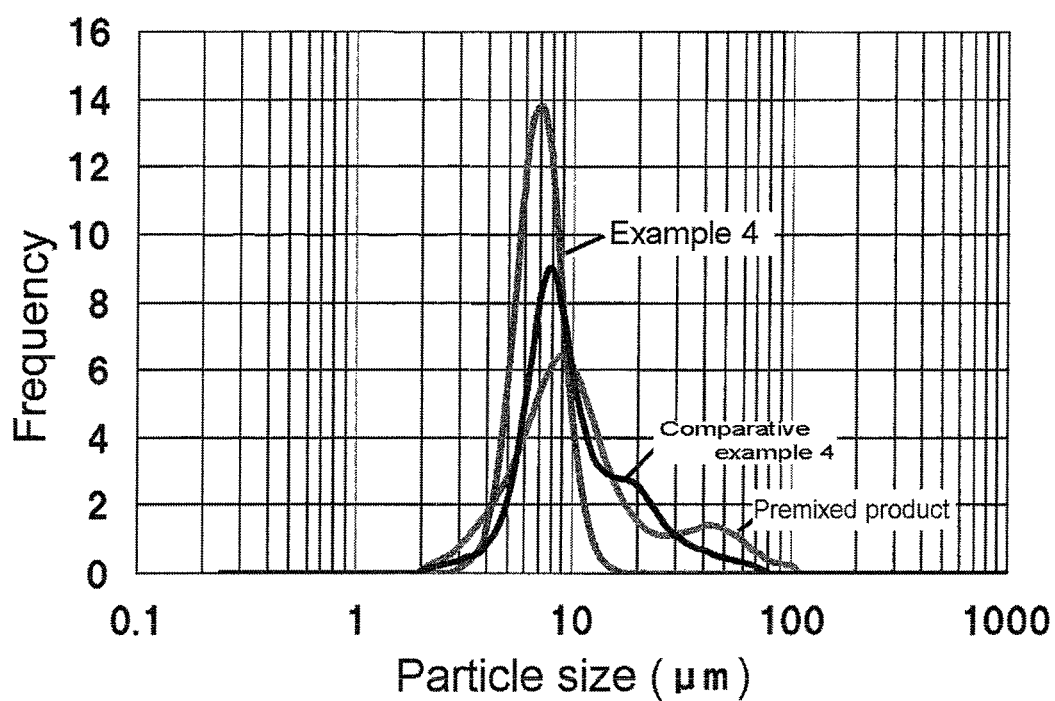
FIG. 3 is a chart for the particle size distribution for the mixture of powder component/oil component, obtained in Example 4 and Comparative Example 4, and the distribution for the premixed product.

As shown in FIG. 3, the agglomeration of powder components is caused in the premixed product, and the particle size distribution is very broad. In the mixture of Comparative Example 4, in which a pulverizer was used, the particle size at the peak is small compared with the premixed product. Thus, it is understood that the agglomeration of powder components is slightly suppressed.

On the other hand, it was clarified in the mixture of Example 4, in which a facing rotor type mixing apparatus was used, that the particle size at the peak is smaller and the particle size distribution is very sharp. That is, when a facing rotor type mixing apparatus was used, the powder component, in a suppressed agglomeration state, was uniformly mixed with the oil component. Thus, it is understood that a mixture in which the powder surface was uniformly coated, nearly in the primary particle state, with the oil component was obtained.

Subsequently, the present inventors have investigated the improvement mechanism of the production method of the present invention. Powder cosmetics (foundation) were produced using the formulations shown in the following Table 11. Then, the practical characteristics and the impact resistance of the obtained various powder cosmetics were evaluated according to the above-described evaluation criteria.

TABLE 11

| | Production Example | | | | | | | |
|---|---|---|---|---|---|---|---|---|
| Foundation | 1-1 | 1-2 | 1-3 | 2-1 | 2-2 | 2-3 | 3-1 | 3-2 |
| Silicone-treated sericite | 12 | 12 | 12 | 12 | 12 | 12 | 12 | 12 |
| Silicone-treated mica | Balance | Balance | Balance | Balance | Balance | Balance | Balance | Balance |
| Silicone-treated talc | 23 | 23 | 23 | 23 | 23 | 23 | 23 | 23 |
| Silicone-treated titanium oxide | 12 | 12 | 12 | 12 | 12 | 12 | 12 | 12 |
| Aluminum stearate-treated fine titanium oxide | 4 | 4 | 4 | 4 | 4 | 4 | 4 | 4 |
| Silicone-treated red iron oxide | 1.2 | 1.2 | 1.2 | 1.2 | 1.2 | 1.2 | 1.2 | 1.2 |
| Silicone-treated yellow iron oxide | 2.5 | 2.5 | 2.5 | 2.5 | 2.5 | 2.5 | 2.5 | 2.5 |
| Silicone-treated black iron oxide | 0.9 | 0.9 | 0.9 | 0.9 | 0.9 | 0.9 | 0.9 | 0.9 |
| Polyurethane powder | 5 | 5 | 10 | 5 | 5 | 10 | 2 | 5 |
| Fine zinc oxide | 2 | 2 | 2 | 2 | 2 | 2 | 2 | 2 |
| Parabene | Q.S. | Q.S. | Q.S. | Q.S. | Q.S. | Q.S. | Q.S. | Q.S. |
| Dimethylpolysiloxane (5 mPa · s) | 3 | 6 | 9 | 3 | 6 | 9 | 3 | 3 |
| Hydrogenated isopolybutene (20000 mPa · s) | 2 | 2 | 2 | 2 | 2 | 2 | 2 | 2 |
| Methylphenylpolysiloxane | 3 | 3 | 3 | 3 | 3 | 3 | 3 | 3 |
| Octyl methoxycinnamate | 3 | 3 | 3 | 3 | 3 | 3 | 3 | 3 |
| Polyether silicone | 1 | 1 | 1 | 1 | 1 | 1 | 1 | 1 |
| Antioxidant | Q.S. | Q.S. | Q.S. | Q.S. | Q.S. | Q.S. | Q.S. | Q.S. |
| Perfume | Q.S. | Q.S. | Q.S. | Q.S. | Q.S. | Q.S. | Q.S. | Q.S. |

TABLE 11-continued

| Foundation | Production Example | | | | | | | |
|---|---|---|---|---|---|---|---|---|
| | 1-1 | 1-2 | 1-3 | 2-1 | 2-2 | 2-3 | 3-1 | 3-2 |
| Production method | Premix with Henschel mixer ↓ Mix two times with facing rotor type mixing apparatus ↓ Press-mold into plastic inner tray | | | Premix with Henschel mixer ↓ Slurry by dispersing into ethanol ↓ Press-mold with vacuum suction | | | Premix with Henschel mixer ↓ Mix two times with pulverizer ↓ Press-mold into plastic inner tray | |
| Feeling of particulate fineness | ◎ | ◎ | ◎ | Δ | Δ | Δ | Δ | Δ |
| Moist feeling | ○ | ○ | ○ | ○ | Δ | Δ | Δ | ○ |
| Smoothness | ◎ | ◎ | ◎ | ○ | Δ | Δ | Δ | ○ |
| Powdery texture | ○ | ○ | ○ | ○ | ○ | ○ | Δ | ○ |
| Uniform finish | ◎ | ◎ | ◎ | Δ | Δ | Δ | ○ | Δ |
| Long-lasting property | ○ | ○ | ○ | ○ | ○ | ○ | Δ | Δ |
| Impact resistance (times) | 10 | 12 | 10 | 5 | 12 | 11 | 10 | 4 |

As shown in the above Table 11, when the powder cosmetics are produced by blending 2 mass % of elastic powder in the conventional dry method (Production Example 3-1), the usabilities such as the moist feeling and smoothness were poor, but the impact resistance was excellent. On the other hand, when 5 mass % of elastic powder was blended in the same dry method (Production Example 3-2), somewhat good results were shown in usability; however, the evaluation results in the uniform finish and the impact resistance were poor.

From the results of the Production Examples 3-1 and 3-2, it is clarified that if the powder cosmetics are produced by blending a large amount of elastic powder in the conventional dry method, the impact resistance will be poor.

Subsequently, the above-described evaluations were carried out by appropriately varying the blending quantities of elastic powder and the oil component in the conventional wet method. As a result, when 5 mass % of the elastic powder and a small amount of the oil component were blended (Production Example 2-1), the usability such as smoothness was excellent, but the impact resistance was poor because of a large amount of the elastic powder, and a satisfactory uniform finish could not be achieved because of the low content of the oil component. On the other hand, when the blending quantity of the elastic powder was maintained at 5 mass % and the blending quantity of the oil component was increased (Production Example 2-2), good results were obtained for impact resistance because of the good retention of the molded shape. However, the usability was poor because of a large amount of oil. When 10 mass % of the elastic powder was blended, similar evaluation results were obtained (Production Example 2-3).

When the powder cosmetics were produced using the same formulations as above and by the production method of the present invention (Production Examples 1-1 to 1-3), the powder cosmetics excellent in impact resistance could be obtained, unlike the above cases in which the conventional production methods were used, even when some elastic powder was blended. In addition, it was clarified that an excellent feeling in use could be achieved without blending a large amount of oil component. As a result, it became possible to allow a sufficient amount of elastic powder to be contained without blending a large amount of oil component. Thus, the extensibility became good, and it was clarified that the feeling in use such as moist feeling, and smoothness would also become excellent.

Thus, when the powder cosmetics were produced by blending a large amount of elastic powder in the conventional dry method, a problem of impact resistance was generated. Even when the problem in impact resistance was solved by blending a large amount of oil in the wet method, the usability was poor because of a large amount of oil.

However, if the production method of the present invention is used, a large amount of elastic powder, which could not be blended in the conventional production method, is allowed to be blended, resulting in excellent usability. In addition, even if the blending quantity of oil component is small, the homogenization of the powder component and the oil component can be carried out well and the powder cosmetics with high impact resistance can be produced. Thus, there is little limitation in the blending quantity of the oil component, and the powder cosmetics with various feelings in use can be prepared.

Subsequently, the present inventors have investigated the preferable blending quantity of elastic powder used in the present invention.

TABLE 12

| Foundation | Production Example | | | | | | |
|---|---|---|---|---|---|---|---|
| | 4-1 | 4-2 | 4-3 | 4-4 | 4-5 | 4-6 | 4-7 |
| Silicone-treated sericite | 12 | 12 | 12 | 12 | 12 | 12 | 12 |
| Silicone-treated mica | Balance | Balance | Balance | Balance | Balance | Balance | Balance |
| Silicone-treated talc | 23 | 23 | 23 | 23 | 23 | 23 | 23 |
| Silicone-treated titanium oxide | 12 | 12 | 12 | 12 | 12 | 12 | 12 |
| Aluminum stearate-treated fine titanium oxide | 4 | 4 | 4 | 4 | 4 | 4 | 4 |
| Silicone-treated red iron oxide | 1.2 | 1.2 | 1.2 | 1.2 | 1.2 | 1.2 | 1.2 |
| Silicone-treated yellow iron oxide | 2.5 | 2.5 | 2.5 | 2.5 | 2.5 | 2.5 | 2.5 |
| Silicone-treated black iron oxide | 0.9 | 0.9 | 0.9 | 0.9 | 0.9 | 0.9 | 0.9 |
| Silicone elastic powder*[2] | 0 | 2 | 5 | 10 | 15 | 20 | 25 |

TABLE 12-continued

| Foundation | Production Example | | | | | | |
|---|---|---|---|---|---|---|---|
| | 4-1 | 4-2 | 4-3 | 4-4 | 4-5 | 4-6 | 4-7 |
| Spherical polymethyl methacrylate powder | 5 | 5 | 5 | 5 | 5 | 5 | 5 |
| Fine zinc oxide | 2 | 2 | 2 | 2 | 2 | 2 | 2 |
| Parabene | Q.S. | Q.S. | Q.S. | Q.S. | Q.S. | Q.S. | Q.S. |
| Dimethylpolysiloxane (5 mPa · s) | 3 | 3 | 3 | 3 | 3 | 3 | 3 |
| Hydrogenated isopolybutene (20000 mPa · s) | 2 | 2 | 2 | 2 | 2 | 2 | 2 |
| Methylphenylpolysiloxane | 3 | 3 | 3 | 3 | 3 | 3 | 3 |
| Octyl methoxycinnamate | 3 | 3 | 3 | 3 | 3 | 3 | 3 |
| Polyether silicone | 1 | 1 | 1 | 1 | 1 | 1 | 1 |
| Antioxidant | Q.S. | Q.S. | Q.S. | Q.S. | Q.S. | Q.S. | Q.S. |
| Perfume | Q.S. | Q.S. | Q.S. | Q.S. | Q.S. | Q.S. | Q.S. |
| Production method | Premix with Henschel mixer ↓ Mix two times with facing rotor type mixing apparatus ↓ Press-mold into plastic inner tray | | | | | | |
| Feeling of particulate fineness | ⊚ | ⊚ | ⊚ | ⊚ | ⊚ | ⊚ | ○ |
| Moist feeling | ○ | ○ | ○ | ○ | ○ | ○ | Δ |
| Smoothness | Δ | ○ | ⊚ | ⊚ | ⊚ | ⊚ | ○ |
| Powdery texture | ○ | ○ | ○ | ○ | ○ | ○ | Δ |
| Uniform finish | ○ | ○ | ⊚ | ⊚ | ⊚ | ○ | ○ |
| Long-lasting property | ○ | ○ | ○ | ○ | ○ | ○ | Δ |
| Impact resistance (times) | 15 | 13 | 10 | 12 | 10 | 8 | 6 |

From the results in the above Table 12, when the elastic powder was not blended at all (Production Example 4-1) or 2 mass % thereof was blended (Production Example 4-2), the impact resistance was excellent and the feeling in use was good; however, the smoothness and uniform finish were somewhat poor. When the blending quantity of elastic powder exceeded 25 mass % (Production Example 4-7), the usability was good, but the impact resistance was somewhat poor.

Thus, when the production method of the present invention was used, the especially preferable range of elastic powder that can be blended in the powder cosmetic was clarified to be 5.0 to 20.0 mass %. According to the production method of the present invention, a large amount of elastic powder can be blended while realizing excellent usability and high impact resistance.

Subsequently, the present inventors have investigated the improvement mechanism of the production method of the present invention and the preferable blending quantity of fluorine-treated powder used in the present invention. Powder cosmetics (foundation) of Production Examples 5-1 to 5-6 and 6-1 to 6-5 were produced, by the production method of the present invention, using the formulations shown in the following Table 13. Then, the practical characteristics and the impact resistance of the obtained various powder cosmetics were evaluated according to the above-described evaluation criteria.

TABLE 13

| Foundation | Production Example | | | | | | | | | | |
|---|---|---|---|---|---|---|---|---|---|---|---|
| | 5-1 | 5-2 | 5-3 | 5-4 | 5-5 | 5-6 | 6-1 | 6-2 | 6-3 | 6-4 | 6-5 |
| 1H,1H,2H,2H-perfluorooctyl triethoxysilane (5%)-treated talc | 0 | 5 | 20 | 40 | 65 | 75 | 0 | 5 | 20 | 40 | 60 |
| Silicone-treated talc | Balance | Balance | Balance | Balance | Balance | Balance | Balance | Balance | Balance | Balance | Balance |
| Silicone-treated titanium oxide | 10 | 10 | 10 | 10 | 10 | 10 | 10 | 10 | 10 | 10 | 10 |
| Aluminum stearate-treated fine titanium oxide | 4 | 4 | 4 | 4 | 4 | 4 | 4 | 4 | 4 | 4 | 4 |
| Silicone-treated red iron oxide | 1.2 | 1.2 | 1.2 | 1.2 | 1.2 | 1.2 | 1.2 | 1.2 | 1.2 | 1.2 | 1.2 |
| Silicone-treated yellow iron oxide | 2.5 | 2.5 | 2.5 | 2.5 | 2.5 | 2.5 | 2.5 | 2.5 | 2.5 | 2.5 | 2.5 |
| Silicone-treated black iron oxide | 0.9 | 0.9 | 0.9 | 0.9 | 0.9 | 0.9 | 0.9 | 0.9 | 0.9 | 0.9 | 0.9 |
| Polyurethane powder | 5 | 5 | 5 | 5 | 5 | 5 | 5 | 5 | 5 | 5 | 5 |
| Fine zinc oxide | 2 | 2 | 2 | 2 | 2 | 2 | 2 | 2 | 2 | 2 | 2 |
| Parabene | Q.S. | Q.S. | Q.S. | Q.S. | Q.S. | Q.S. | Q.S. | Q.S. | Q.S. | Q.S. | Q.S. |
| Dimethylpolysiloxane (5 mPa · s) | 3 | 3 | 3 | 3 | 3 | 3 | 3 | 3 | 3 | 3 | 3 |
| Hydrogenated isopolybutene (20000 mPa · s) | 3 | 3 | 3 | 3 | 3 | 3 | 3 | 3 | 3 | 3 | 3 |
| Methylphenylpolysiloxane | 3 | 3 | 3 | 3 | 3 | 3 | 3 | 3 | 3 | 3 | 3 |
| Octyl methoxycinnamate | 2 | 2 | 2 | 2 | 2 | 2 | 2 | 2 | 2 | 2 | 2 |
| Sorbitan sesquiisostearate | 1 | 1 | 1 | 1 | 1 | 1 | 1 | 1 | 1 | 1 | 1 |
| Antioxidant | Q.S. | Q.S. | Q.S. | Q.S. | Q.S. | Q.S. | Q.S. | Q.S. | Q.S. | Q.S. | Q.S. |
| Perfume | Q.S. | Q.S. | Q.S. | Q.S. | Q.S. | Q.S. | Q.S. | Q.S. | Q.S. | Q.S. | Q.S. |

TABLE 13-continued

| Foundation | Production Example | | | | | | | | | | |
|---|---|---|---|---|---|---|---|---|---|---|---|
| | 5-1 | 5-2 | 5-3 | 5-4 | 5-5 | 5-6 | 6-1 | 6-2 | 6-3 | 6-4 | 6-5 |
| Production method | Premix with Henschel mixer ↓ Mix two times with facing rotor type mixing apparatus ↓ Press-mold into plastic inner tray | | | | | | Premix with Henschel mixer ↓ Mix two times with pulverizer ↓ Press-mold into plastic inner tray | | | | |
| Feeling of particulate fineness | ⊚ | ⊚ | ⊚ | ⊚ | ⊚ | ⊚ | ◯ | ◯ | Δ | Δ | X |
| Moist feeling | ◯ | ◯ | ◯ | ◯ | ◯ | Δ | ◯ | Δ | Δ | Δ | Δ |
| Smoothness | ◯ | ◯ | ◯ | ◯ | ◯ | Δ | ◯ | Δ | Δ | X | X |
| Powdery texture | ◯ | ◯ | ◯ | ◯ | ◯ | ◯ | ◯ | Δ | Δ | X | X |
| Uniform finish | ⊚ | ⊚ | ⊚ | ⊚ | ⊚ | ◯ | ◯ | Δ | Δ | Δ | X |
| Long-lasting property | ◯ | ⊚ | ⊚ | ⊚ | ⊚ | ⊚ | Δ | Δ | ◯ | ◯ | ◯ |
| Impact resistance (times) | 10 | 10 | 12 | 14 | 15 | 13 | 7 | 7 | 7 | 7 | 7 |

As shown in the right column of the above Table 13, the blending quantity of fluorine-treated powder was suitably varied in the conventional dry method. When 5 mass % or higher fluorine-treated powder was blended, the long-lasting property was excellent, but the usability was poor because of the poor adhesion to the skin (Production Examples 6-2 to 6-5). When no fluorine-treated powder was blended in the same dry method, the long-lasting property was poor (Production Example 6-1).

On the other hand, as shown in the left column of the above Table 6, when the powder cosmetics were produced with the use of the facing rotor type mixing apparatus of the present invention, the products were different from those produced with the use of the conventional production method. Even when some fluorine-treated powder (5 to 75 mass %) was blended, the powder agglomeration did not take place, a uniform finish was achieved, and powder cosmetics with excellent usability were obtained (Production Examples 5-2 to 5-6).

Thus, the upper limit of the preferable blending quantity of fluorine-treated powder blended into the powder cosmetic, which is obtained by the production method of the present invention, is not restricted in particular. However, the blending quantity is preferably 5 to 75 mass %, and more preferably 20 to 65 mass %.

Subsequently, the present inventors have investigated the preferable blending quantity of high-viscosity oil.

TABLE 14

| Foundation | Production Example | | | | | | | | | |
|---|---|---|---|---|---|---|---|---|---|---|
| | 7-1 | 7-2 | 7-3 | 7-4 | 7-5 | 7-6 | 8-1 | 8-2 | 8-3 | 8-4 |
| 1H,1H,2H,2H-perfluorooctyl triethoxysilane (5%)-treated talc | 40 | 40 | 40 | 40 | 40 | 40 | 40 | 40 | 40 | 40 |
| Silicone-treated talc | Balance | Balance | Balance | Balance | Balance | Balance | Balance | Balance | Balance | Balance |
| Silicone-treated titanium oxide | 10 | 10 | 10 | 10 | 10 | 10 | 10 | 10 | 10 | 10 |
| Aluminum stearate-treated fine titanium oxide | 4 | 4 | 4 | 4 | 4 | 4 | 4 | 4 | 4 | 4 |
| Silicone-treated red iron oxide | 1.2 | 1.2 | 1.2 | 1.2 | 1.2 | 1.2 | 1.2 | 1.2 | 1.2 | 1.2 |
| Silicone-treated yellow iron oxide | 2.5 | 2.5 | 2.5 | 2.5 | 2.5 | 2.5 | 2.5 | 2.5 | 2.5 | 2.5 |
| Silicone-treated black iron oxide | 0.9 | 0.9 | 0.9 | 0.9 | 0.9 | 0.9 | 0.9 | 0.9 | 0.9 | 0.9 |
| Polyurethane powder | 5 | 5 | 5 | 5 | 5 | 5 | 5 | 5 | 5 | 5 |
| Fine zinc oxide | 2 | 2 | 2 | 2 | 2 | 2 | 2 | 2 | 2 | 2 |
| Parabene | Q.S. | Q.S. | Q.S. | Q.S. | Q.S. | Q.S. | Q.S. | Q.S. | Q.S. | Q.S. |
| Dimethylpolysiloxane (5 mPa · s) | 3 | 3 | 3 | 3 | 3 | 3 | 3 | 3 | 3 | 3 |
| Hydrogenated isopolybutene (20000 mPa · s) | 0 | 0.1 | 0.5 | 5 | 10 | 15 | 0 | 0.5 | 5 | 10 |
| Methylphenylpolysiloxane | 3 | 3 | 3 | 3 | 3 | 3 | 3 | 3 | 3 | 3 |
| Octyl methoxycinnamate | 2 | 2 | 2 | 2 | 2 | 2 | 2 | 2 | 2 | 2 |
| Sorbitan sesquiisostearate | 1 | 1 | 1 | 1 | 1 | 1 | 1 | 1 | 1 | 1 |
| Antioxidant | Q.S. | Q.S. | Q.S. | Q.S. | Q.S. | Q.S. | Q.S. | Q.S. | Q.S. | Q.S. |
| Perfume | Q.S. | Q.S. | Q.S. | Q.S. | Q.S. | Q.S. | Q.S. | Q.S. | Q.S. | Q.S. |
| Production method | Premix with Henschel mixer ↓ Mix two times with facing rotor type mixing apparatus ↓ Press-mold into plastic inner tray | | | | | | Premix with Henschel mixer ↓ Mix two times with pulverizer ↓ Press-mold into plastic inner tray | | | |
| Feeling of particulate fineness | ⊚ | ⊚ | ⊚ | ⊚ | ⊚ | Δ | Δ | Δ | Δ | X |
| Moist feeling | ◯ | ◯ | ◯ | ◯ | ◯ | Δ | Δ | Δ | Δ | X |
| Smoothness | Δ | ◯ | ⊚ | ◯ | ◯ | Δ | Δ | Δ | X | X |
| Powdery texture | Δ | ◯ | ◯ | ◯ | ◯ | ◯ | Δ | Δ | X | X |
| Uniform finish | Δ | ⊚ | ⊚ | ⊚ | ◯ | Δ | Δ | Δ | Δ | X |
| Long-lasting property | ◯ | ⊚ | ⊚ | ⊚ | ⊚ | ⊚ | ◯ | ◯ | ◯ | ◯ |
| Impact resistance (times) | 7 | 10 | 12 | 14 | 14 | 14 | 5 | 6 | 8 | 10 |

As shown in the right column of the above Table 14, when the fluorine-treated powder was fixed at 40 mass % and the blending quantity of high-viscosity oil was suitably varied in the conventional dry method, the impact resistance was somewhat improved by increasing the amount of high-viscosity oil, but the usability was poor (Production Examples 8-1 to 8-4). On the other hand, as shown in the left column of the above Table 7, when the powder cosmetics were produced with the use of the facing rotor type mixing apparatus of the present invention, the products were different from those produced with the use of the conventional production method. Even when the fluorine-treated powder was fixed at 40 mass % and 0.1 to 10 mass % of high-viscosity oil was blended, similarly to the above-described formulation, the powder agglomeration did not take place, a uniform finish was achieved, and powder cosmetics with excellent usability were obtained (Production Examples 7-2 to 7-5).

However, when the blending quantity of high-viscosity oil exceeded 10 mass %, the uniform finish and the usability tended to be somewhat poor (Production Example 7-6).

Thus, it was clarified that the blending quantity of the high-viscosity oil that is blended into the powder cosmetic obtained by the production method of the present invention is preferably 0.1 to 10 mass %, and more preferably 0.5 to 5 mass %.

| Example 11: Foundation | mass % |
| --- | --- |
| Sericite | 10 |
| Synthetic mica | Balance |
| Zinc decyltrisiloxane carboxylate-coated talc | 5 |
| Spherical silicone powder | 3 |
| (Trefil E-506S: manufactured by Dow Corning Toray Co., Ltd.) | |
| Spherical silicone powder | 5 |
| (Tospearl 2000B: manufactured by Toshiba silicone Co., Ltd.) | |
| Spherical silicone powder | 5 |
| (Silicone powder KSP300: manufactured by Shin-Etsu Chemical Co., Ltd.) | |
| Spherical porous silica | 2 |
| (Sunsphere L-51: manufactured by Asahi Glass Co., Ltd.) | |
| Titanium oxide | 11 |
| Red interference pearl pigment | 2 |
| Zinc oxide | 2 |
| Red iron oxide | 0.8 |
| Yellow iron oxide | 2 |
| Black iron oxide | 0.1 |
| Spherical nylon powder | 4 |
| Dimethylpolysiloxane (5 mPa · s) | 3 |
| Dimethylpolysiloxane (5000 mPa · s) | 2 |
| Squalane | 3 |
| Petrolatum | 2 |
| Sorbitan sesquiisostearate | 1 |
| Paraben | Q.S. |
| Antioxidant | Q.S. |
| Perfume | Q.S. |

(Production method) The oil component was added to the powder component of the formulation and mixed with a Henschel mixer for a fixed amount of time, and then they were mixed two times with a facing rotor type mixing apparatus shown in FIG. 1 and press-molded into a plastic inner tray.

| Example 12: White powder (Pressed powder) | mass % |
| --- | --- |
| Zinc decyltrisiloxane carboxylate-coated talc | 10 |
| Synthetic mica | Balance |
| Zinc oxide | 5 |
| Red interference pearl pigment | 3 |
| Fine titanium oxide | 3 |

| Example 12: White powder (Pressed powder) | mass % |
| --- | --- |
| Spherical silicone powder | 3 |
| (Trefil E-506S: manufactured by Dow Corning Toray Co., Ltd.) | |
| Spherical silicone powder | 5 |
| (Tospearl 2000B: manufactured by Toshiba silicone Co., Ltd.) | |
| Spherical silicone powder | 5 |
| (Silicone powder KSP300: manufactured by Shin-Etsu Chemical Co., Ltd.) | |
| Spherical porous silica | 2 |
| (Sunsphere L-51: manufactured by Asahi Glass Co., Ltd.) | |
| Dimethylpolysiloxane (5000 mPa · s) | 2 |
| Diisostearyl malate (2000 mPa · s) | 1 |
| Squalane | 1 |
| Ester oil | 2 |
| Paraben | Q.S. |
| Antioxidant | Q.S. |
| Perfume | Q.S. |

(Production method) The oil component is added to the powder component of the formulation and mixed with a Henschel mixer for a fixed amount of time, and then they were mixed two times with a facing rotor type mixing apparatus shown in FIG. 1 and press-molded into a plastic inner tray.

| Example 13: Foundation | mass % |
| --- | --- |
| Sericite | 10 |
| Synthetic mica | Balance |
| Zinc decyltrisiloxane carboxylate-coated talc | 5 |
| Spherical silicone powder | 3 |
| (Trefil E-506S: manufactured by Dow Corning Toray Co., Ltd.) | |
| Spherical silicone powder | 5 |
| (Tospearl 2000B: manufactured by Toshiba silicone Co., Ltd.) | |
| Spherical silicone powder | 5 |
| (Silicone powder KSP300: manufactured by Shin-Etsu Chemical Co., Ltd.) | |
| Spherical porous silica | 2 |
| (Sunsphere L-51: manufactured by Asahi Glass Co., Ltd.) | |
| Silicone-treated titanium oxide | 15 |
| Red interference pearl pigment | 2 |
| Zinc oxide | 2 |
| Silicone-treated red iron oxide | 0.8 |
| Silicone-treated yellow iron oxide | 2 |
| Silicone-treated black iron oxide | 0.1 |
| Spherical nylon powder | 4 |
| 1H,1H,2H,2H-perfluorooctyltriethoxysilane (5%)/ Formula(II) copolymer (2%)-treated talc | 20 |
| 1H,1H,2H,2H-perfluorooctyltriethoxysilane (5%)/ Formula(II) copolymer (2%)-treated barium Sulfate | 10 |
| Dimethylpolysiloxane (5 mPa · s) | 3 |
| Dimethylpolysiloxane (5000 mPa · s) | 2 |
| Squalane | 3 |
| Petrolatum | 1 |
| Di(phytosteryl/behenyl) dimer dilinoleate | 2 |
| Sorbitan sesquiisostearate | 0.2 |
| Chlorphenesin | Q.S. |
| Antioxidant | Q.S. |
| Perfume | Q.S. |

(Production method) The oil component was added to the powder component of the formulation and mixed with a Henschel mixer for a fixed amount of time, and then they were mixed two times with a facing rotor type mixing apparatus shown in FIG. 1 and press-molded into a plastic inner tray.

| Example 14: White powder (Pressed powder) | mass % |
| --- | --- |
| Zinc decyltrisiloxane carboxylate-coated talc | 10 |
| Synthetic mica | Balance |
| Silica silylate | 5 |

-continued

| Example 14: White powder (Pressed powder) | mass % |
|---|---|
| Zinc oxide | 5 |
| Red interference pearl pigment | 3 |
| Fine titanium oxide | 3 |
| Spherical silicone powder | 3 |
| (Trefil E-506S: manufactured by Dow Corning Toray Co., Ltd.) | |
| Spherical silicone powder | 5 |
| (Tospearl 2000B: manufactured by Toshiba silicone Co., Ltd.) | |
| Spherical silicone powder | 5 |
| (Silicone powder KSP300: manufactured by Shin-Etsu Chemical Co., Ltd.) | |
| Spherical porous silica | 2 |
| (Sunsphere L-51: manufactured by Asahi Glass Co., Ltd.) | |
| 1H,1H,2H,2H-perfluorooctyltriethoxysilane (5%)/ | 40 |
| Formula(II) copolymer (5%)-treated talc | |
| Hydrogenated isopolybutene (20000 mPa · s) | 0.5 |
| Diisostearyl malate (2000 mPa · s) | 1 |
| Squalane | 1 |
| Ester oil | 1 |
| Paraben | Q.S. |
| Antioxidant | Q.S. |
| Perfume | Q.S. |

(Production method) The oil component was added to the powder component of the formulation and mixed with a Henschel mixer for a fixed amount of time, and then they were mixed two times with a facing rotor type mixing apparatus shown in FIG. 1 and press-molded into a plastic inner tray.

Powder cosmetics obtained in the above Examples 11 to 14 were excellent in various practical characteristics such as the feeling of particulate fineness, moist feeling, smoothness, powdery texture, and uniform finish. In addition, the impact resistance was also good.

What is claimed is:

1. A production method of a powder cosmetic comprising:
   mixing raw materials comprising 65 to 97 mass % of powder component and 3 to 35 mass % of an oil component as a binder with a mixing apparatus, wherein the mass % is based on the total amount of powder cosmetic,
      wherein the mixing apparatus is a facing rotor type mixing apparatus having a first rotor with a plurality of blades and a second rotor with a plurality of blades in a mixing chamber, in which the first rotor and the second rotor face each other and have respective rotating shafts on same axis line in an approximately horizontal direction, and
      wherein mixing comprises feeding raw materials into an introduction opening on a side of the mixing chamber proximate to the first rotor and rotating the first rotor and the second rotor in the same or opposite directions to each other to obtain a mixture in which the surface of the powder component is uniformly coated with the oil component without the agglomeration of the powder component, and
   discharging the mix from a discharge opening on a side of the mixing chamber proximate to the second rotor.

2. The production method of a powder cosmetic according to claim 1, wherein mixing comprises rotating the first rotor and the second rotor of the facing rotor type mixing apparatus in opposite directions to each other.

3. The production method of a powder cosmetic according to claim 1, wherein the powder component comprises fluorine compound-treated powder.

4. The production method of a powder cosmetic according to claim 2, wherein the powder component comprises fluorine compound-treated powder.

5. The production method of a powder cosmetic according to claim 1, wherein the powder component comprises 5.0 to 20.0 mass % of elastic powder with respect to the total amount of powder cosmetic.

6. The production method of a powder cosmetic according to claim 2, wherein the powder component comprises 5.0 to 20.0 mass % of elastic powder with respect to the total amount of powder cosmetic.

7. The production method of a powder cosmetic according to claim 3, wherein the powder component comprises 5.0 to 20.0 mass % of elastic powder with respect to the total amount of powder cosmetic.

8. The production method of a powder cosmetic according to claim 1, wherein the oil component comprises 0.1 to 10 weight % of an oil with a viscosity of 100 to 50000 mPa·s with respect to the total amount of powder cosmetic.

9. The production method of a powder cosmetic according to claim 2, wherein the oil component comprises 0.1 to 10 weight % of an oil with a viscosity of 100 to 50000 mPa·s with respect to the total amount of powder cosmetic.

10. The production method of a powder cosmetic according to claim 5, wherein the oil component comprises 0.1 to 10 weight % of an oil with a viscosity of 100 to 50000 mPa·s with respect to the total amount of powder cosmetic.

11. A production method of a powder cosmetic comprising:
    mixing raw materials comprising 65 to 97 mass % of a powder component including 5 to 75 mass % fluorine compound-treated powder and 3 to 35 mass % of an oil component including 0.1 to 10 mass % oil with a viscosity of 100 to 50000 mPa·s as a binder using a mixing apparatus, wherein the mass % is based on the total amount of powder cosmetic,
       wherein the mixing apparatus is a facing rotor type mixing apparatus having a first rotor with a plurality of blades and a second rotor with a plurality of blades in a mixing chamber, in which the first rotor and the second rotor face each other and have respective rotating shafts on same axis line in an approximately horizontal direction, and
       wherein mixing comprises feeding raw materials into an introduction opening on a side of the mixing chamber proximate to the first rotor and rotating the first rotor and the second rotor in the same or opposite directions to each other to obtain a mixture in which the surface of the powder component is uniformly coated with the oil component without the agglomeration of the powder component, and
    discharging the mix from a discharge opening on a side of the mixing chamber proximate to the second rotor.

12. The production method of a powder cosmetic according to claim 11, wherein mixing comprises rotating the first rotor and the second rotor of the facing rotor type mixing apparatus in opposite directions to each other.

13. The production method of a powder cosmetic according to claim 11, wherein the powder component comprises elastic powder.

14. The production method of a powder cosmetic according to claim 12 wherein the powder component comprises elastic powder.

15. A production method of a powder cosmetic comprising:
    mixing raw materials comprising 65 to 97 mass % of powder component comprising 8.0 to 15.0 mass % of elastic powder and 3 to 35 mass % of an oil component as a binder using a mixing apparatus, wherein the mass % is based on the total amount of powder cosmetic wherein the mixing apparatus is a facing rotor type mixing apparatus having a first rotor with a plurality of blades and a second rotor with a plurality of blades in a mixing chamber, in which the first rotor and the second rotor face each other and have respective rotating shafts on same axis line in an approximately horizontal direction, and wherein mixing comprises feeding raw materials into an introduction opening on a side of the mixing chamber proximate to the first rotor and rotating the first rotor and the second rotor in the same or opposite directions to each other to obtain a mixture in which the surface of the powder component is uniformly coated with the oil component without the agglomeration of the powder component, and discharging the mix from a discharge opening on a side of the mixing chamber proximate to the second rotor.

16. The production method of a powder cosmetic according to claim 15, wherein mixing comprises rotating the first rotor and the second rotor of the facing rotor type mixing apparatus in opposite directions to each other.

17. The production method of a powder cosmetic according to claim 15, wherein the powder component comprises fluorine compound-treated powder.

18. The production method of a powder cosmetic according to claim 15, wherein the oil component comprises 0.1 to 10 weight % of an oil with a viscosity of 100 to 50000 mPa·s with respect to the total amount of powder cosmetic.

* * * * *